(12) United States Patent
Rieck et al.

(10) Patent No.: US 8,271,403 B2
(45) Date of Patent: Sep. 18, 2012

(54) METHOD AND APPARATUS FOR AUTOMATIC COMPARISON OF DATA SEQUENCES USING LOCAL AND GLOBAL RELATIONSHIPS

(75) Inventors: Konrad Rieck, Berlin (DE); Pavel Laskov, Berlin (DE); Klaus-Robert Mueller, Berlin (DE); Patrick Duessel, Berlin (DE)

(73) Assignee: Fraunhofer-Gesellschaft zur Förderung der Angewandten Forschung e.V., München (DE)

( * ) Notice: Subject to any disclaimer, the term of this patent is extended or adjusted under 35 U.S.C. 154(b) by 923 days.

(21) Appl. No.: 12/096,126
(22) PCT Filed: Dec. 8, 2006
(86) PCT No.: PCT/EP2006/012063
§ 371 (c)(1),
(2), (4) Date: Jun. 4, 2008
(87) PCT Pub. No.: WO2007/131545
PCT Pub. Date: Nov. 22, 2007

(65) Prior Publication Data
US 2009/0024555 A1    Jan. 22, 2009

(30) Foreign Application Priority Data

Dec. 9, 2005 (EP) .................................. 05077873
Oct. 19, 2006 (EP) .................................. 06090193

(51) Int. Cl.
*G06F 11/00* (2006.01)
(52) U.S. Cl. ........................................................ 706/12
(58) Field of Classification Search ............... 706/12, 706/45, 20
See application file for complete search history.

(56) References Cited

U.S. PATENT DOCUMENTS
4,084,260 A    4/1978  Fleming et al.

FOREIGN PATENT DOCUMENTS
JP    484271 A    3/1992

OTHER PUBLICATIONS

Rieck et al. "Efficient Algorithms for Similarity Measures over Sequential Data: A Look Beyond Kernels", DAGM (2006), LNCS 4174, pp. 374-383, Springer-Verlag Berlin Heidelberg.
M. Anderberg, "Cluster Analysis for Applications: Chapter 4: Measures of Association Among Variables", Academic Press, Inc., New York, NY, USA, 1973, p. 70-97.
Eskin et al. "Applications of Data Mining in Computer Security: Chapter 4: A Geometric Framework for Unsupervised Anomaly Detection: Detecting Intrusions in Unlabeled Data", Kluwer, 2002, p. 77-101.
D. Gusfield, "Algorithmus on strings, trees, and sequences: Linear-Time Construction of Suffix Trees", Cambridge University Press, 1997, p. 94-121.
D. Knuth, "The art of computer programming", vol. 3, Addison-Wesley, 1973, p. 480-501.

(Continued)

*Primary Examiner* — David Vincent
(74) *Attorney, Agent, or Firm* — The Webb Law Firm

(57) ABSTRACT

The invention is concerned with a method and an apparatus for automatic comparison of at least two data sequences characterized in—an evaluation of a local relationship between any pair of subsequences in two or more sequences; —an evaluation of a global relationship by means of aggregation of the evaluations of said local relationships.

8 Claims, 12 Drawing Sheets

OTHER PUBLICATIONS

J. Shawe-Taylor and N. Cristianini, "Kernel methods for pattern analysis", Cambridge University Press, 2004, p. 344-396.
R. Sokal and P. Sneath; "Principles of Numerical Taxonomy", W. H. Freeman and Company, San Francisco, CA, USA, 1963, Chapter 6, p. 123-155.
W. B. Cavnar et al. "N-Gram-Based Text Categorization", In Proc. SDAIR, p. 161-175, Las Vegas, NV, USA, Apr. 1994.
S. Forrest et al. "A Sense of Self for Unix Processes", In Proc. IEEE Symposium on Security and Privacy, p. 120-128, Oakland, CA, USA, 1996.
A. K. Ghosh et al. "Learning Program Behavior Profiles for Intrusion Detection", In Proc. USENIX, p. 51-62, Santa Clara, CA, USA, Apr. 1999.
Hofmeyr et al. "Intrusion Detection using Sequences of System Calls", Journal of Computer Security, 1998, p. 151 ff.
Marceau "Characterizing the Behavior of a Program Using Multiple-Length N-grams", In Proc. NSPW, p. 101-110, 2000.
Leslie et al. "The spectrum kernel: A string kernel for SVM protein classification", In Proc. Pacific Symp. on Biocomputing, 2002, p. 566-575.
Lodhi et al. "Text Classification using String Kernels", Journal of Machine Learning Research 2, 2002, p. 419-444.
Vishwanathan et al. "Fast Kernels for String and Tree Matching", In Kernels and Bioinformatics, MIT Press, 2004.
Leslie et al. "Fast String Kernels using Inexact Matching for Protein Sequences" Journal of Machine Learning Research 5, 2004, p. 1435-1455.
C. Watkins "Dynamic Alignment Kernels", In A.J. Smola et al., editors; Advances in Large Margin Classifiers, p. 39-50, Cambridge, MA, 2000, MIT Press.
K. Wang et al. "Anomalous Payload-based Network Intrusion Detection", In Proc. RAID, 2004.
Leslie et al. "Mismatch String Kernels for SVM Protein Classification", Bioinformatics 1, 2003.
C. H. Teo et al. "Fast and Space Efficient String Kernels using Suffix Arrays", In Proceedings, 23rd ICMP, p. 939-936, ACM Press, 2006.
Rousu et al. "Efficient Computation of Gapped Substring Kernels on Large Alphabets", Journal of Machine Learning Research 6, 2005, p. 1323-1344.
M. V. Mahoney et al. "PHAD: Packet Header Anomaly Detection for Identifying Hostile Network Traffic", Technical Report CS-2001, Florida Institute of Technology.
W. Lee et al. "Learning Patterns from Unix Process Execution Traces for Intrusion Detection", In Proc. AAAI, p. 50-56, 1997, USA.
Kruegel et al. "Service Specific Anomaly Detection for Network Intrusion Detection", In Proc. Symposium on Applied Computing, p. 201-208, 2002.
Wang et al.; "Anomalous Payload-Based Worm Detection and Signature Generation"; Recent Advances in Intrusion Detection Lecture Notes in Computer Science; LNCS, Sep. 7, 2005; pp. 227-246; vol. 3858, Springer-Verlag, BE.
Leonid Portnoy et al., "Intrusion Detection with Unlabeled Data Using Clustering," Proceedings of ACM CSS Workshop on Data Mining Applied to Security (DMSA-2001), 2001, pp. 1-14, ACM, Philadelphia, USA.

(b) Comparison of hash tables (a) Hash tables (b) Comparison of tries (a) Tries (b) Traversal of a GST (a) Generalized suffix tree (GST)

(b) Results for DNA application (a) Results for network application

METHOD AND APPARATUS FOR AUTOMATIC COMPARISON OF DATA SEQUENCES USING LOCAL AND GLOBAL RELATIONSHIPS

BACKGROUND OF THE INVENTION

1) Field of the Invention

The automatic comparison of data in sequences is a commonly encountered task in computer science, natural science and engineering problems. Data sequences in the context of the present invention correspond to sets of consecutive objects which can be tested for equality or, more generally, for similarity or dissimilarity.

2) Description of the Related Art

Typical examples of data sequences are sequences of symbols, images, text (e.g. ASCII characters), genetic data, proteins, bytes, binary data or abstract tokens.

Two data sequences containing any of these kinds of objects can be compared with each other, so that a similarity (or dissimilarity) value between both can be computed. In extension of this idea, more than two data sequences can be compared with each other, so that a matrix comprising pairwise similarity values is obtained.

SUMMARY OF THE INVENTION

It is the purpose of the present invention to provide a robust method and apparatus for comparing data sequences and calculating similarity values.

The method and apparatus for data sequence comparison proceeds in embodiments by
(a) representing data sequences as sets of contained subsequences and
(b) computing similarity measures over the numbers of occurrences of contained subsequences included in either both or only in one of the two sequences. The embodiments of the method and the apparatus supports various measures of similarity and different schemes for selecting subsequences to consider.

BRIEF DESCRIPTION OF THE DRAWINGS

In the following, the invention is described in more detail with reference to the embodiments shown in the figures.

Figure 7:
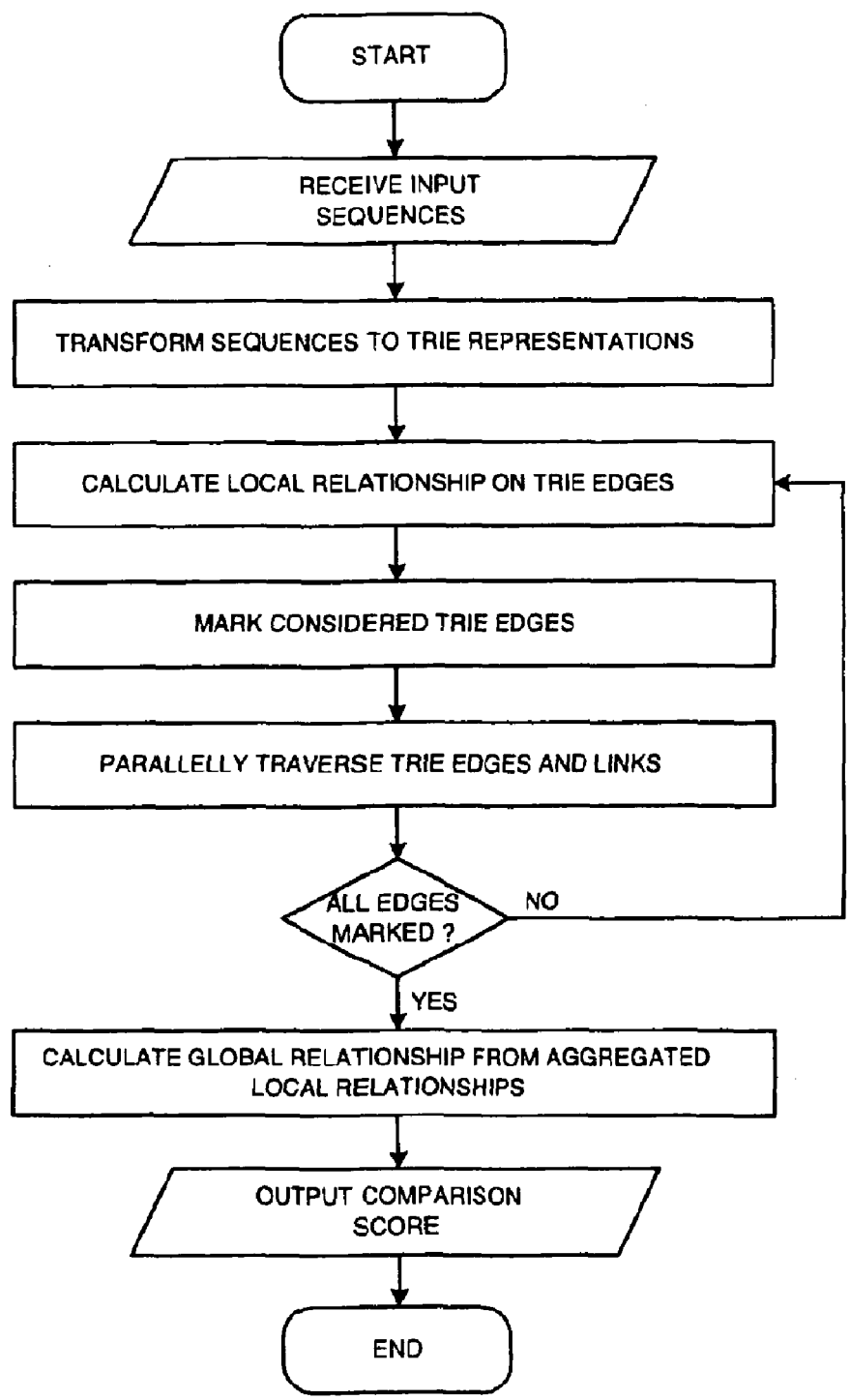
FIG. 7 shows a flow chart of one embodiment of the invention involving tries.

Possible embodiments of the invention will be described in connection with the Chapters A to D being parts of the description of the present patent application. The embodiments differ in the particular data structures used for storage and comparison of the data sequences. A flow chart of one embodiment of the invention involving tries is shown in FIG. 7.

Different modes for selecting subsequences for comparison are presented in Chapters C and D. Given a data sequence there are three common modes for representing its context in terms of subsequences:

(a) Words. Sequences are partitioned into non-overlapping subsequences which are delimited by a set of delimiter symbols. In natural language texts these symbols correspond to white spaces and punctuation symbols. For other applications different definitions of such symbols are possible.

(b) N-grams. Sequences are represented by contained subsequences of length n, which overlap by at most (n−1) symbols. N-grams are commonly used in cases where structural information such as delimiters is unknown or difficult to model, e.g. in analysis of DNA sequences.

(c) All subsequences. In this most general case sequences are represented by all contained subsequences. Thus, a sequence of m symbols is mapped to the set of m(m−1)/2 contained subsequences, which also cover all possible n-grams and words.

All these three modes are supported by embodiments of the present invention.

Building on these sets of contained subsequences, two sequences x and y can be compared by considering the number of occurrences of contained subsequences defined according to any of the three modes described above.

The main feature of the disclosed method is contribution of all appropriate subsequences contained either in both or in one of the two sequences. A generic procedure is presented for aggregation of such contributions in similarity measures. A similarity measure s used for calculating a similarity value between two data sequences x and y in the present invention is represented in a generic form as $$s(x, y) = \bigoplus_{w \in L} m(\varphi_w(x), \varphi_w(y))$$

where $\oplus$ is the aggregation operator over all subsequences w in a set L corresponding to the chosen subsequence selection mode and m is the match function. The function $\phi_w(x)$ returns a quantitative measure for the occurrences of the subsequence w present in the data sequence x, e.g. a count or frequency value.

Different embodiments of similarity measures differ in the definitions of the function m and the operator $\oplus$:

(a) The match function m is a measure of local relationship i.e. similarity or dissimilarity between contained subsequences in terms of $\phi_w(x)$ and $\phi_w(y)$. The function can be e.g. the absolute difference or the squared difference between the occurrences of subsequences in the data sequences. However, other formulations measuring similarity as in the case of the linear kernel in Chapters D are possible. Further examples are given in Tables 8 and 9 of Chapters C and Table 14 of Chapters D.

(b) The global aggregation operator ⊕ stands for a plurality of possible operations for evaluation of the global relationship i.e. the aggregation of the local relationships expressed by the match function. This operator is applied to the set L of subsequences corresponding to a chosen subsequence selection mode. Examples for such operators are given in Tables 8 and 9 of Chapters C and Table 14 of Chapters D.

Various measures of similarity and dissimilarity can be expressed in the above formulation by deriving corresponding definitions for the match function m and the aggregation operator ⊕.

As one example the Euclidian distance function $$\sum_{i=1}^{n}(x_i - y_i)^2$$

can be expressed in terms of ⊕ and m, where the match function corresponds to $(x_i - y_i)^2$ and the aggregation operator ⊕ would be the summation. In another example, the Chebyshev distance is expressed by using the max functions as ⊕ and the absolute difference $|x_i - y_i|$ as match function m. Further embodiments for similarity measures are described in context with Tables 8 and 9 in Chapters C and Table 14 in Chapters D.

A listing of similarity measures suitable for the generic representation of m and ⊕, such as the Euclidean, Chebyshev and Manhattan distance or the similarity coefficient by Jaccard, Czekanowski or Kulszynski, are given in Tables 5 to 7 of Chapters C and Tables 12 to 13 of Chapters D.

Beside the generic formulation of similarity measures over contained subsequence, a second component in the method and apparatus for data sequence comparison is the utilization of particular data structures for efficient computation.

Following is a list of suitable data structures and descriptions of procedures for their application to computation of similarity measures over sequential data:

(a) Hash tables. Each data sequence x is transformed into a hash table, that contains the values $\phi_w(x)$ corresponding to subsequences w of x according to a chosen selection mode. Computation of a similarity measure is carried out by looping over the bins of two hash tables corresponding to two sequences x and y, calculating the match function and aggregation operator over $\phi_w(x)$ and $\phi_w(y)$. The corresponding procedure is given in Section 3.1 of Chapters C.

(b) Tries. Each data sequence x is transformed into a Trie data structure. For a sequence generated from a set of objects of size m, a Trie is an m-ary tree containing all subsequences corresponding to a chosen selection mode. The nodes of a Trie are augmented with the values $\phi_w(x)$ for each subsequence w in x. Computation of a similarity measure is carried out by traversing two tries corresponding to two sequences x and y in parallel and retrieving $\phi_w(x)$ and $\phi_w(y)$ in the Trie nodes for calculating the match function and aggregation operator. An procedure for the trie-based comparison is given in Section 3.2 of Appendix C. A concrete embodiment as part of a network intrusion detection application is described in Appendix A.

(c) Suffix trees and suffix arrays. Each data sequence x is transformed into a suffix tree or a suffix array. A suffix tree is a tree structure in which every path from the root to a leave corresponds to a suffix of the considered data sequence. Similarly to a Trie the values $\phi_w(x)$ for subsequences w in x are stored in nodes of the suffix tree depending on a selection scheme. Computation of a similarity measure is carried out by a multi-pass traversal of two suffix trees corresponding to two sequences x and y. During the first pass of each suffix tree subsequences represented by nodes are identified and marked, which are contained in both sequences. During the second pass of each suffix tree appropriate contributions $\phi_w(x)$ and $\phi_w(y)$ from marked and unmarked nodes are aggregated for computation of a similarity measure. Alternatively the comparison procedure can be realized using suffix arrays instead of suffix trees. A suffix array contains all suffixes of a sequence in lexicographically sorted order. In combination with two auxiliary arrays, the longest common prefix and suffix link array, the disclosed method based on suffix trees can be carried out using suffix arrays.

(d) Generalized suffix tree. A generalized suffix tree extends a suffix tree by comprising all suffixes of a set of data sequences. The approach differs from the embodiments (a)-(c), as the data sequences to be compared are represented by a single data structure. During a post-order traversal of the generalized suffix tree the values $\phi_w(x)$ for each subsequence w in x can be aggregated. Computation of a similarity measure is carried out during the post-order traversal by calculating the match function and aggregation operator. In the case of the generalized suffix tree the subsequence selection mode is realized by assigning weights to each node in the tree in an appropriate way. Similarly to the suffix array method, the disclosed embodiment can also be realized using a generalized suffix array. A procedure for the comparison algorithm is given in Appendix D.

All four embodiments of the present invention based on different data structures can be extended to support computation of similarity measures for more than two sequences. In the cases of (a)-(c) the method is extended by transforming a set of m sequences to a set of m corresponding data structures. A matrix of similarity values is obtained by calculating the resulting m2 pairwise similarities between the data sequences. The embodiment (d) is inherently able to compute similarity measures for multiple data sequences. Once a set of sequences has been transformed to the generalized suffix tree representation, a single post-order traversal is sufficient for computation of all pairwise similarity values.

We propose a novel representation of language models for network intrusion detection that uses a trie data structure to efficiently store n-grams and words extracted from TCP connections. This representation allows one to compute a variety of similarity measures over TCP connections and to apply unsupervised anomaly detection algorithms suitable for detection of unknown attacks.

Results of experiments conducted on the DARPA 1999 dataset and on our own dataset PESIM 2005 demonstrate the importance of higher-order n-grams (as opposed to 1-grams) for detection of network attacks. Our method is also suitable for language models based on words, which are more amenable to practical security applications than n-gram models. An implementation of our system has achieved detection accuracy of 80-100% at 0.2% false-positive rate on 27 recent attacks in HTTP, FTP and SMTP traffic.

DETAILED DESCRIPTION OF THE INVENTION

1. Introduction

Detection of unknown attacks is a long-standing issue on a wish-list of security practitioners. While it is often claimed that current applications and infrastructures for tracking vulnerabilities and their exploits provide adequate protection by means of attack signatures, there exist numerous examples of unknown attacks, notably worms [e.g. 38] and zero-day exploits [e.g. 1], that have defeated signature-based defenses. Furthermore, it often does not suffice for a signature to be available—deployed signatures must be kept up-to-date by security administrators in order to keep their systems safe.

Discussion about unknown attacks has been carried out in various parts of the intrusion detection community. For misuse detection, it centers around the issues of making signatures more generic—and capable of at least not to be fooled by mutations of known attacks [37, 22, 15, 30, 7, 33]. There is, however, a growing consensus that genuinely novel attacks can be only detected by anomaly detection tools, at a cost of having to deal with false positives which may also be valid anomalies.

A large amount of previous work has been done on anomaly detection in network traffic [e.g. 41, 42, 16, 26, 25, 9]. The main hurdle on the way to its acceptance in practice is a high rate of false-positives. Most of the previous approaches do not deliver sufficient accuracy in the promille range of false-positive rates, which is what practitioners need (and which may still be too high). Hence further improvements of anomaly-based intrusion detection techniques are highly desirable.

Apart from methodical differences, the main issue underlying various anomaly detection approaches is the features they operate on. Some early approaches considered only packet header information or statistical properties of sets of packets or connections [25, 19]. This information has proved to be useful for detection of certain kinds of malicious activity, e.g. probes and port scans, yet it usually does not suffice to detect attacks that exploit semantic vulnerabilities of application-layer protocols and their implementations.

In this paper we present a general technique for detection of unknown network attacks which uses similarity measures over language models, such as n-grams and words, for analysis of byte streams in TCP connections. The n-gram representation has been long known in the literature on host-based IDS [e.g. 10, 14, 43, 27, 12]. Recently, some techniques of network intrusion detection have been proposed in which n-gram models are applied for anomaly detection over packet payloads or connection contents [16, 42, 41]. It has been demonstrated that such models can be quite effective in detecting attacks that do not manifest themselves in packet headers.

The reason why n-grain models are successful in description of content-based discriminative features can be seen by comparing protocols and natural languages. The content of both is characterized by rich syntax and semantics, and discrimination between different categories is only possible in terms of syntactic and semantic constructs. For both protocols and natural languages, extensive effort has been made to describe important concepts by means of rules, only to find out that rules can hardly encompass the full generality of underlying content. Protocols and natural languages possess grammatic structure, yet recovery of this structure is stymied by uncertainty and ambiguity.

In view of the linguistic analogy, one can see that identification of (unknown) misuse patterns amounts to learning (unknown) concepts in an underlying protocol language. Hence it is clearly promising to apply the machinery of natural language processing to network intrusion detection. While doing so one must, however, beware a technical challenge of network-based IDS: high-speed and high-volume data. For all previously reported experimental results with n-gram models of network traffic n=1 was used, which indirectly points out the main technical problem with applying this model: how can statistical features of n-grams, the number of which can be large, be efficiently computed and compared?

To address this problem we propose a novel representation of n-grams based on tries. This representation allows one to compute, in linear time, a large variety of similarity measures on n-grams, e.g. Manhattan, Euclidean and Canberra distances, Kulczynski and Czekanowski similarity coefficients, as well as various kernel functions. Using these similarity measures, one can apply unsupervised anomaly detection algorithms to detect unusual events. As a result, anomaly detection using our technique is extremely easy to deploy in practice: once connected to a network, our system performs anomaly detection without any training or extensive configuration, converging to a stable regime after a short period of learning a profile of normal data.

As a proof of concept, we experimentally evaluate our methods on the DARPA 1999 IDS dataset and on our own dataset created by a penetration testing expert. Unlike previous work using the DARPA 1999 dataset, in which usually the whole spectrum of attacks is considered, we focus on attacks against application-layer protocols whose increasing complexity breeds a large amount of vulnerabilities. Exploits of such vulnerabilities often enable attackers to obtain privileges sufficient for severe abuse of network services; therefore, attacks against application-layer protocols are most dangerous in the sense of practical security. The list of attacks present in our experiments is given in Tables 1 and 2.

The results of our experiments demonstrate that n-grams can convey a valuable information for detection of unknown attacks. As a distinction from previous work, we have observed that for some attacks important discriminative features are contained in n-grams of length n>1. On the other hand, our experiments show that it may be difficult to determine an optimal length of n-gram models in advance, an effect known from research in natural language processing. To remedy this problem, we extend our models beyond n-grams to words, and show that such models yield accuracy that is only marginally lower than the accuracy of experimentally optimal n-gram models. Finally, we establish that the proposed methods significantly outperform a recent version of an open-source IDS Snort with a standard signature set.

2. Related Work

Quite naturally, language models have been first developed by researchers in the fields of information retrieval and natural language processing—several decades before their relevance for intrusion detection was discovered. As early as mid-sixties, character n-grams were used for error correction in optical character recognition [32]. Application of n-grams to text categorization was pioneered by Suen [40] and was followed by a large body of subsequent research [e.g. 4, 3, 35]. The main idea of n-gram-based approaches is to compute frequencies of all subsequences containing n consecutive characters (n-grams) and to define similarity measures based on these frequencies. Despite the exponential number of n-grams in an alphabet, only a linear number of them is present in a given character string. Efficient comparison of n-grams can be done by means of hashing. Various similarity measures were used to compare n-gram frequencies, e.g. the inner product between frequency vectors [4] or Manhattan and Canberra distances [3]. Recent approaches to text categorization advocate the use of kernel functions as similarity measures, which allow one to incorporate contextual information [44, 21, 24].

Re-discovery of n-gram models in the realm of host-based IDS began in the mid-nineties with the seemingly ad-hoc "sliding window" approach of Forrest et al. [10]. In modern terminology this approach can be classified as n-gram-based supervised anomaly detection. The main idea of Forrest et al. was to create a database of all possible n-grams in system call traces resulting from normal operation of a program. Traces with a large degree of binary mismatch to the database were flagged as anomalous. In the ensuing work these ideas were extended through application of Hidden Markov Models [43], feed-forward and recursive neural networks [12] and rule induction algorithms [20]. A comprehensive evaluation of these approaches showed that all of the above methods could effectively detect anomalous behavior of intrusions in the datasets they were tested on [43].

Application of n-gram models for network-based IDS originated in the idea of using a limited form of a byte histogram of packet payloads for statistical tests of anomaly [16]. A more advanced model was proposed by Wang and Stolfo, in which histograms of packet payloads are used to detect anomalous packets whose payload histograms have large Mahalanobis distance to histograms learned from normal data [42]. This approach can be easily seen as a particular case of an n-gram approach with n=1. The peculiarity of the method of Wang and Stolfo is that packet payload distributions are conditioned on packet lengths; merging of adjacent models is used to reduce an overall model size. The anomalous payload detection sensor PAYL using this method has been successfully applied to detect worms in network traffic [41].

3. N-Gram Tries

As a reader can easily see from a brief review of related work, different intuitions lead to a simple language model—namely, n-grams—which captures a coarse syntax of an underlying language in a way sufficient to discriminate between normal and anomalous events. A key to utilizing such models in anomaly detection algorithms is to provide a set of similarity measures that possess desirable discriminating properties. It should be noted that a large variety of similarity (and dissimilarity) measures is available from literature, some of which are reviewed in A.2. Therefore it is highly desirable to be able to draw upon these measures without alteration of data structures and algorithms for computation of n-gram histograms.

To see why an underlying data structure is crucial for an efficient implementation of similarity measures, some technical issues must be discussed. A classical scheme of storing and comparing n-gram histograms makes use of a hash table [e.g. 4]. It allows to store l−n+1 (in the worst-case) distinct n-grams present in a character stream in an hash table of size k, the relation between l and k depending on parameters of a hash function. Insertion into a hash table takes constant time, and a simple comparison of two hash tables takes O(k), again, provided that a hash function is good enough to avoid too many collisions. Since the hash table elements are not ordered, computation of any similarity measure necessitates a loop over all k table elements.

Figure 1:
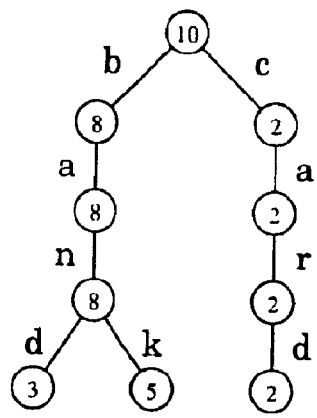
FIG. 1 shows an example of storing a set of words in a trie structure.

We propose to store the n-grams collected from a byte stream in a trie [5, 11]. Insertion into a trie takes O(n log |Σ|) where |Σ| is the size of the alphabet (in our case 256). An example of storing a set of words {"bank", "band", "card"} is shown in FIG. 1. Each node of a trie is augmented to contain a counter which is incremented every time a node is hit during insertion of an n-gram into the trie. The counts in FIG. 1 correspond to the presence of 3 "band"s, 5 "bank"s and 2 "card"s in an input stream.

Computation of similarity measures over n-gram tries can be done by expressing a target measure as an operator over matching functions: $d(x,Y) = \oplus_{s,t}^{TrieX,Y} m(s,t)$, where a matching function can be a match $m^+(s,t)$, a local mismatch $m^-(s)$ and a global mismatch $m^*(s)$ function. Using a suitable definition of $m^+$, $m^-$ and $m^*$, a variety of measures can be defined. For example, the Manhattan distance between two tries is obtained with $m^+(s,t)=|c_s-c_t|$, $m^-(s)=m^*(s)=|c_s|$, where $c_i$ is a count of a respective node in the trie. A decisive advantage of tries-over hash tables takes place when comparing two byte streams of different lengths, say $l_1 \ll l_2$. For a trie representation a match can be performed in $O(\min(l_1,l_2))$; for a hash table a match always requires $O(k) \approx O(\max(l_1,l_2))$ operations.

In the application of a trie data structure to n-gram analysis of network traffic we consider streams of incoming bytes of assembled TCP connections. For every connection, a trie is built which contains a compressed representation of all n-grams in the incoming byte stream. We then feed tries into an unsupervised learning algorithm which performs detection using a given similarity measure. Thus our approach is similar to the "per connection" model of Wang and Stolfo [42], except that we do not perform conditioning over payload length and clustering of adjacent bins.

Figure 2:
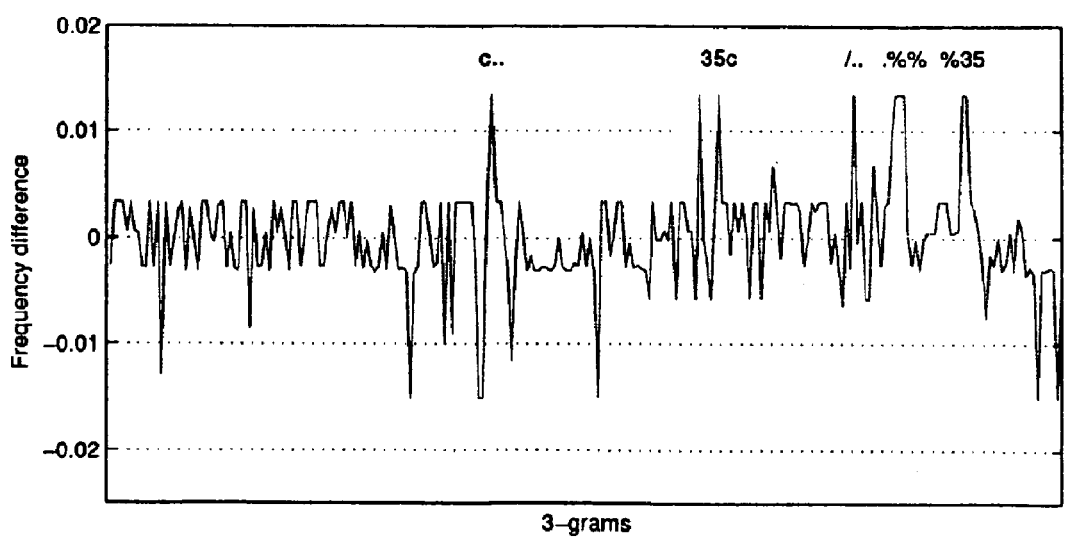
FIG. 2 shows frequency differences of 3-grams for an IIS unicode attack and normal HTTP traffic.

The way n-grams can characterize network attacks in TCP connections can be best illustrated by an example. FIG. 2 shows the differences between 3 gram frequencies of an IIS unicode attack and normal HTTP traffic. Due to the large possible space of 3-grams the plot is limited to 3 grams present in the IIS unicode attack.

Several positive peaks indicate a high deviation from normal traffic and correspond to typical 3-grams of the attack, e.g. "35c", "/.." and "%35". These 3-grams manifest an essential pattern of the unicode attack "%%35c" which is converted by a vulnerable IIS server to "%5c" (ASCII code 0x35 corresponds to "5") and finally interpreted as backslash (ASCII code 0x5c). The corresponding fragment of the attack is shown below.

```
GET
/scripts/..%%35c../..%%35c../..%%35c../..%%35c../..%%35c../..%%35c..
    /winnt/system/cmd.exe?/c+dir+c:
```

4. Unsupervised Anomaly Detection On N-Gram Tries

Unsupervised anomaly detection is particularly suitable to the practical needs of intrusion detection, as it spares an administrator from the task of collecting data representative of normal activity. An unsupervised anomaly detection algorithm can be directly applied to a stream of data and is supposed to effectively discriminate between normal and anomalous patterns "on-the-fly". Furthermore, no extensive configuration of the algorithm or training using manually labeled data is required.

Because of its favorable properties, unsupervised anomaly detection has gained significant interest in recent work on intrusion detection [e.g. 34, 9, 18]. The algorithms for unsupervised anomaly detection exploit differences in geometric features of anomalies and normal data. These algorithms can explore local properties, e.g. single-linkage clustering [34] and our new k-nearest neighbor method Zeta [citation omitted], or global properties, e.g. simplified Mahalanobis distance [42] and quarter-sphere SVM [17]. (A brief summary of these four algorithms used in our work is presented in A.1).

Anomaly detection algorithms usually require a similarity measure between pairs of objects which essentially defines a geometric representation of data. As it was shown in Section 3 a variety of similarity measures can be defined on n-gram tries. In particular, we have examined the following measures: the Canberra distance [8], the "binarized" Manhattan distance, the Czekanowski coefficient [6] and the (second) Kulczynski coefficient [39]. (A brief description of these measures is given in A.2.)

5. Experimental Results

In order to evaluate the proposed n-gram trie representation of network connections with respect to detection performance, and to gain insights into the nature of recovered syntactic information, we conducted experiments on two network traffic datasets. Specifically we are interested to clarify the following open questions:

1. Does increased length of n-grams (n>1) improve detection performance?
2. At what false-positive rate do we detect all instances of attacks present in our data?

We limit our experiments to the popular application-layer protocols HTTP, FTP and SMTP, which constitute a steady target of network attacks in the last decade.

5.1. Datasets

DARPA 1999 Dataset

This well-known dataset from an IDS evaluation conducted by the DARPA in 1999 [23] has been used in numerous publications and can be considered a standard benchmark for evaluation of IDS.

As a preprocessing step, we randomly extracted 1000 TCP connections for each protocol from the first and third weeks of the data corpus representing normal data. We then selected all remote-to-local attacks present in the fourth and fifth weeks of the dataset. Table 1 lists these remote-to-local attacks.

Even though the DARPA 1999 dataset is known to suffer from several flaws and artifacts [26, 28, 29], especially the selection of attacks can be considered antiquated in comparison to modern security threats, it remains the only major dataset on which results can be reproduced.

PESIM 2005 Dataset

In order to overcome the problems of the DARPA 1999 dataset, we generated a second evaluation dataset named PESIM 2005. We deployed a combination of 5 servers using a virtual machine environment. The systems ran two Windows, two Linux and one Solaris operating systems and offered HTTP, FTP and SMTP services.

Normal network traffic for these systems was generated by members of our laboratory. To achieve realistic traffic characteristics we transparently mirrored news sites on the HTTP servers and offered file sharing facility on the FTP servers. SMTP traffic was artificially injected containing 70% mails from personal communication and mailing lists, and 30% spam mails received by 5 individuals. The normal data was preprocessed similarly to the DARPA 1999 dataset by random selection of 1000 TCP connections for each protocol from the data corpus. Attachments were removed from the SMTP traffic.

Attacks against the simulated services were generated by a penetration testing expert using modern penetration testing tools. Multiple instances of 27 different attacks were launched against the HTTP, FTP and SMTP services. The attacks are listed in Table 2. The majority of these attacks is part of the comprehensive collection of recent exploits in the Metasploit framework [31]. Additional attacks were obtained from common security mailing lists and archives, such as Bugtraq and Packetstorm Security. The "PHP script attack" was introduced by the penetration testing expert and exploits insecure input processing in a PHP script.

5.2. Experiments

Best Measure/Detector Configuration

As previously mentioned, similarity measures induce various geometric properties which, in turn, are explored in different ways by anomaly detection methods. Hence, as a first step, we need to roughly establish what combinations of similarity measures and anomaly detectors perform best on n-gram tries for each protocol in question. The candidate similarity measures for this experiment are the Canberra and the "binarized" Manhattan distances, the Czekanowski and the Kulczynski similarity coefficients. The anomaly detectors under consideration are the simplified Mahalanobis distance, the quarter-sphere SVM, the single-linkage clustering and the Zeta anomaly detector.

The following experimental-protocol is implemented. For each measure/detector configuration 10 independent datasets are generated from the corpus. Each dataset is split into a validation partition, used for finding optimal detector parameters, and an independent test partition, used for evaluation of detector accuracy. The evaluation criterion is the so called area under curve (AUC) which integrates true-positive rates over a certain interval of false-positive rate, in our case [0, 0.1]. The procedure is repeated for values of n from 1 to 8, and the results are averaged over 10 runs and all values of n.

Table 3 lists the best three measure/detector configurations for the HTTP, FTP and SMTP protocols on both datasets. For all protocols the configuration with similarity coefficient Kulczynski and local anomaly detector Zeta yields the best overall performance for varying length of n. In the remaining experiments we fix the measure/detector configuration to this setup.

Varying N-Gram Length

Previous results in natural language processing and host-based IDS indicate that the optimal n-gram length may vary for different applications [24, 10]. We now investigate if the same observation holds for n-gram models of TCP connections.

Figure 3:
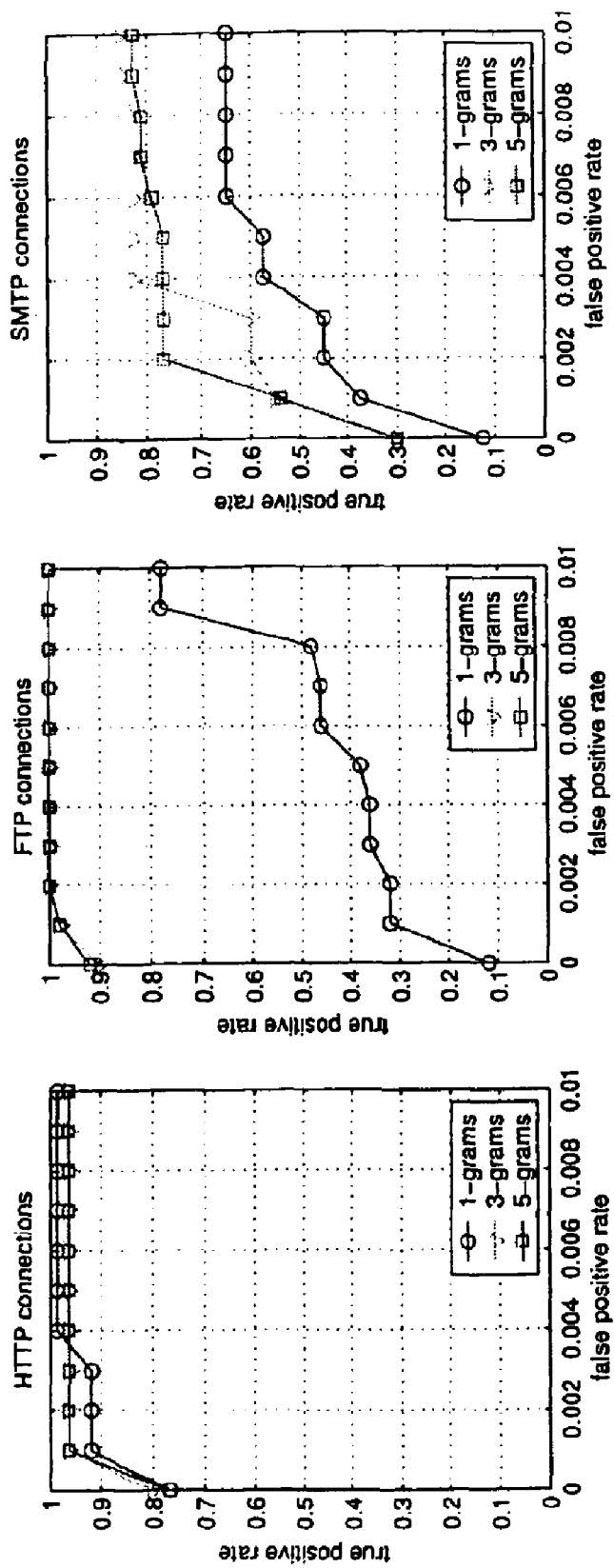
FIG. 3 shows ROC graphs for 1-, 3- and 5-grams (DARPA 1999).
Figure 4:
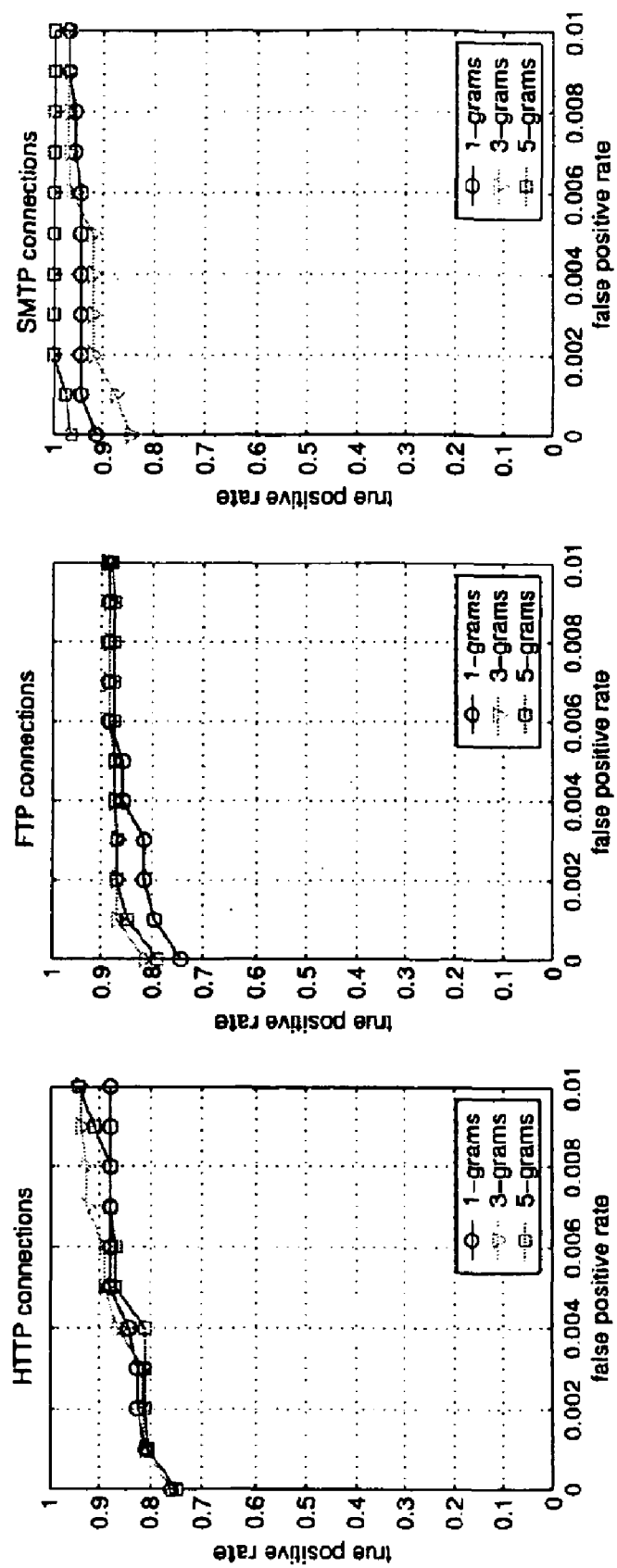
FIG. 4 shows ROC graphs for 1-, 3- and 5-grams (PESIM 2005).

We follow the same setup as in the selection of the optimal measure/detector configuration, except that results of individual values of n are reported using a fixed configuration. The results are shown in FIG. 3 (for the DARPA 1999 dataset) and FIG. 4 (for PESIM 2005 dataset), which display the ROC graphs for selected values of n.

It can be clearly seen that detection performance varies significantly among the values of n for different protocols. In fact, it turns out that each of the three values considered in this experiment is optimal for some protocol—and for a different one in two datasets. Apart from that, the overall accuracy of our approach is very encouraging, especially on the more recent PESIM 2005 dataset. For the best value of n, a detection rate between 80% and 100% was observed at a false-positive rate of 0.2% for the HTTP, FTP and SMTP protocols.

Analysis of Specific Attacks

One is always interested to know how well an IDS detects specific attacks in a dataset. The results of the previous experiment suggest that, in addition, the optimal n-gram length for each attack might be insightful. As criterion for this experiment we considered the minimum false-positive rate at which all instances of an attack are detected. The results are shown in Table 4.

Most of the network attacks from the PESIM 2005 data set are detected with false-positive rates below 1%. Only one attack, the ProFTPd exploit, is poorly recognized. This exploit uploads a malicious file to an FTP server. Since the file content is transferred over a data channel which is not monitored by our system, this attack can only be detected by chance in our setup.

Distribution of optimal n-gram lengths across the attacks reveals two aspects. For several attacks, which are particularly easy to detect, the n-gram length is irrelevant. There exists, however, attacks (easy as well as difficult to detect) for which detection accuracy is significantly better for certain n-gram lengths.

6. From N-Grams To Words

The message from the experiments in the previous section may be somewhat confusing for a practitioner. One can see that longer n-grams bring improvement in detection performance in some cases, on the other hand, no consistency can be found across various attacks and protocols. How should one choose the right n beforehand if attacks are unknown?

The following extension of the n-gram model addresses this concern. Note that the semantics of natural languages is, in fact, defined in terms of words rather than n-grams. Words in a natural language are defined as consecutive character sequences separated by white-space symbols. We conjecture that semantics of application-layer protocols such HTTP, FTP and SMTP can likewise be captured by appropriately defined words. As word separators, the following bytes are proposed:

{CR, LF, TAB, " ", ",", ".", ":", "/", "&"}.

We are now about to discover another remarkable property of the trie representation of n-grams proposed in this paper: it can handle variable-length "grams" without any alteration!

Figure 5:
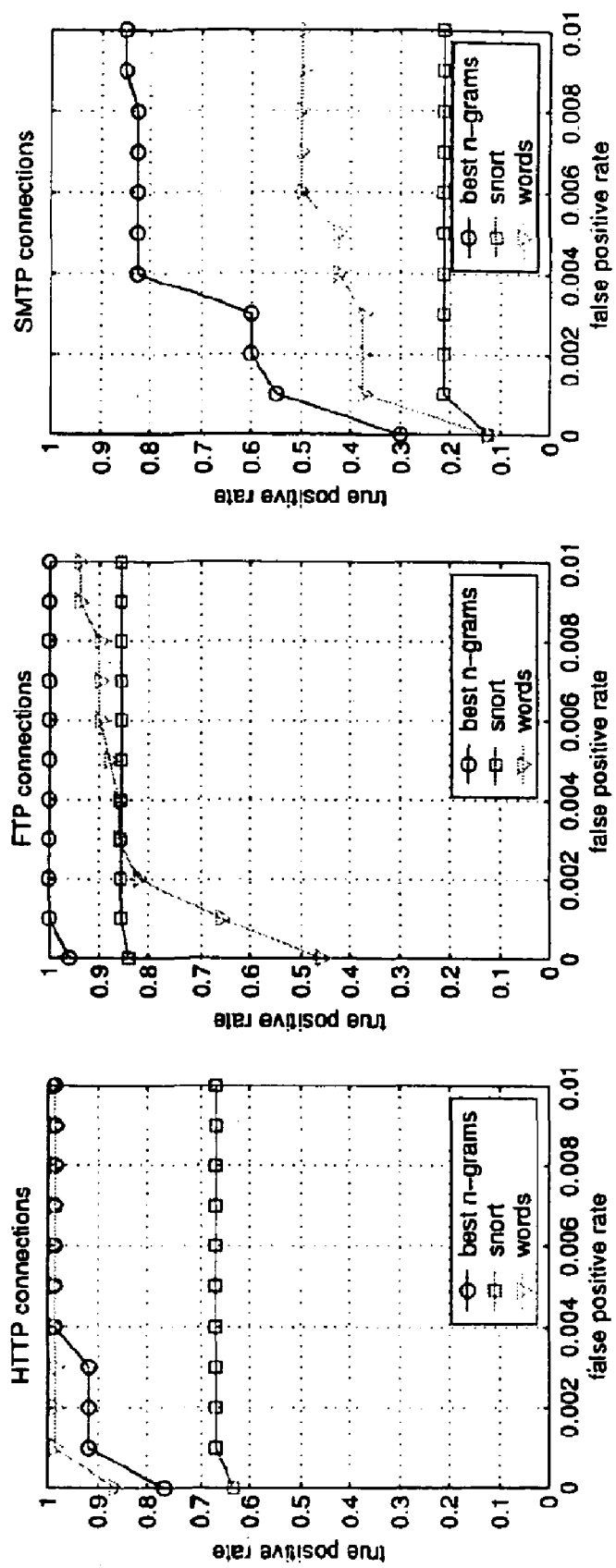
FIG. 5 shows ROC graphs for best n-grams, Snort, and words (DARPA 1999).
Figure 6:
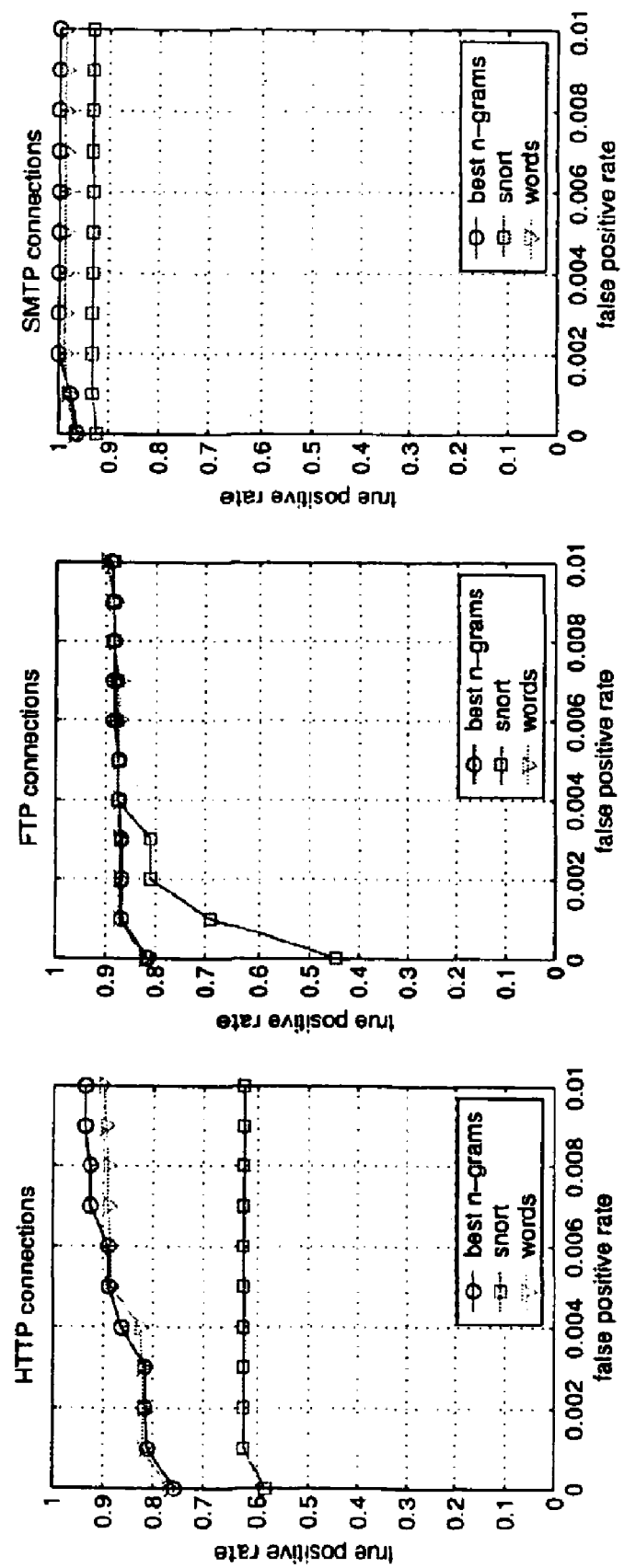
FIG. 6 shows ROC graphs for best n-grams, Snort, and words (PESIM 2005).

We repeat the experiments under the same setup as the experiments on varying n-gram length using the stream of words instead of n-grams. Similarity measures are computed over word frequencies, and the same optimal measure/detector configuration is used. To emphasize the practical focus of this experiment, we compare the results of our-models with the performance of the open-source signature-based IDS Snort [36] (Snort version 2.4.2, released on 28.09.2005 and configured with the default set of rules). The results are shown in FIG. 5 (for the DARPA 1999 dataset) and FIG. 6 (for the PESIM 2005 dataset).

It can be seen that our word-based detector yields the same accuracy on the PESIM 2005 dataset as the best n-gram-based detector. Unfortunately, no consistency can be observed on the DARPA 1999 dataset, which can be attributed to the artificial nature of some attacks present in this dataset. To our surprise, the n-gram and word models significantly outperformed Snort on the PESIM 2005 dataset even though all included attacks except for the "PHP script" were known months before the release date of our Snort distribution.

This result confirms a misgiving that signature-based IDS may fail to discover "fresh" attacks despite a major effort in the security community to maintain up-to-date signature repositories. Noteworthy is the fact that Snort failed in our experiments due to two reasons. Some attacks were not detected because no appropriate signature was present, which is manifested by flat ROC graphs that never reach the 100% level. Other failures occurred due to minor variations in attack syntax. For example, one of the SMTP attacks was not discovered when an attacker replaced the initial "HELO" command with "EHLO", which is allowed by protocol specification and frequently used in practice.

7. Conclusion

We have proposed a novel representation of language models for network intrusion detection that uses tries for efficient storage of n-grams and words extracted from TCP connections. Our representation allows one to compute a variety of similarity and dissimilarity measures over these models in linear time. Being able to compute similarity between TCP connections, we can apply unsupervised anomaly detection algorithms suitable for detection of previously unknown attacks.

Results of experiments conducted on the DARPA 1999 dataset and on our own dataset PESIM 2005 demonstrate the importance of higher-order n-grams (as opposed to 1-grams) for detection of recent network attacks. It is nonetheless difficult to determine the optimal length of n-gram models for particular attacks and protocols. This problem can be alleviated by considering language models based on words, using "white-space" separators appropriate for protocol syntax. The accuracy of unsupervised anomaly detectors based on word models, as investigated in our experiments, is almost identical to the accuracy of the best n-gram models. Furthermore, the system based on our language model significantly outperformed a recent version of the open-source IDS Snort (equipped with a standard set of signatures) in a "plug-and-play" setup.

REFERENCES

[1] CERT Advisory CA-2001-21: Buffer overflow in telnetd. CERT Coordination Center, July 2001.

[2] M. R. Anderberg. *Cluster Analysis for Applications*. Academic Press, Inc., New York, N.Y., USA, 1973.

[3] W. B. Cavnar and J. M. Trenkle. N-gram-based text categorization. In *Proc. SDAIR*, pages 161-175, Las Vegas, Nev., USA., April 1994.

[4] M. Damashek. Gauging similarity with n-grams: Language-independent categorization of text. *Science*, 267(5199):843-848, 1995.

[5] R. de la Briandais. File searching using variable length keys. In *Proc. AFIPS Western Joint Computer Conference*, pages 295-298, 1959.

[6] L. R. Dice. Measure of the amount of ecologic association between species. *Ecology*, 26(3):297-302, 1945.

[7] S. Eckmann, G. Vigna, and R. Kemmerer. STATL: An attack language for state-based intrusion detection. *Journal of Computer Security*, 10(1/2):71-104, 2002.

[8] S. M. Emran and N. Ye. Robustness of canberra metric in computer intrusion detection. In *Proc. IEEE Workshop on Information Assurance and Security*, West Point, N.Y., USA, 2001.

[9] E. Eskin, A. Arnold, M. Prerau, L. Portnoy, and S. J. Stolfo. *Applications of Data Mining in Computer Security*, chapter "A geometric framework for unsupervised anomaly detection: detecting intrusions in unlabeled data". Kluwer, 2002.

[10] S. Forrest, S. A. Hofmeyr, A. Somayaji, and T. A. Longstaff. A sense of self for unix processes. In *Proc. IEEE Symposium on Security and Privacy*, pages 120-128, Oakland, Calif., USA, 1996.

[11] E. Fredkin. Trie memory. *Communications of ACM*, 3(9):490-499, 1960.

[12] A. K. Ghosh, A. Schwartzbard, and M. Schatz. Learning program behavior profiles for intrusion detection. In *Proc. USENIX*, pages 51-62, Santa Clara, Calif., USA, April 1999.

[13] R. W. Hamming. Error-detecting and error-correcting codes. *Bell System Technical Journal* 29(2):147-160, 1950.

[14] S. A. Hofmeyr, S. Forrest, and A. Somayaji. Intrusion detection using sequences of system calls. *Journal of Computer Security*, 6(3):151-180, 1998.

[15] C. Kruegel, E. Kirda, D. Mutz, W. Robertson, and G. Vigna. Polymorphic worm detection using structural information of executables. In *Proc. RAID*, 2005.

[16] C. Kruegel, T. Toth, and E. Kirda. Service specific anomaly detection for network intrusion detection. In *Proc. Symposium on Applied Computing*, pages 201-208, 2002.

[17] P. Laskov, C. Schäfer, and I. Kotenko. Intrusion detection in unlabeled data with quarter-sphere support vector machines. In *Proc. DIMVA*, pages 71-82, 2004.

[18] A. Lazarevic, L. Ertoz, V. Kumar, A. Ozgur, and J. Srivastava. A comparative study of anomaly detection schemes in network intrusion detection, In *Proc. SIAM*, 2003.

[19] W. Lee and S. J. Stolfo. A framework for constructing features and models for intrusion detection systems. In *ACM Transactions on Information and System Security*, volume 3, pages 227-261, November 2001.

[20] W. Lee, S. J. Stolfo, and P. Chan. Learning patterns from unix process execution traces for intrusion detection. In *Proc. AAAI workshop on Fraud Detection and Risk Management*, pages 50-56, Providence, R.I., USA, 1997.

[21] C. Leslie, E. Eskin, and W. S. Noble. The spectrum kernel: a string kernel for SVM protein classification. In *Proc. Pacific Symposium on Biocomputing*, volume 7, pages 564-575, 2002.

[22] Z. Liang and R. Sekar. Automatic generation of buffer overflow attack signatures: An approach based on program behavior models. In *Proc. ACSAC*, 2005. To appear.

[23] R. Lippmann, J. W. Haines, D. J. Fried, J. Korba, and K. Das. The 1999 DARPA off-line intrusion detection evaluation. *Computer Networks*, 34(4):579-595, 2000.

[24] H. Lodhi, C. Saunders, J. Shawe-Taylor, N. Cristianini, and C. Watkins. Text classification using string kernels. *Journal of Machine Learning Research*, 2:419-444, 2002.

[25] M. V. Mahoney and P. K. Chan. PHAD: Packet header anomaly detection for identifying hostile network traffic. Technical Report CS-2001-2, Florida Institute of Technology, 2001.

[26] M. V. Mahoney and P. K. Chan. An analysis of the 1999 DARPA/Lincoln Laboratory evaluation data for network anomaly detection. In *Proc. RAID*, pages 220-237, 2004.

[27] C. Marceau. Characterizing the behavior of a program using multiple-length n-grams. In *Proc. NSPW*, pages 101-110, 2000.

[28] J. McHugh. The 1998 Lincoln Laboratory IDS evaluation. In *Proc. RAID*, pages 145-161, 2000.

[29] J. McHugh. Testing intrusion detection systems: a critique of the 1998 and 1999 DARPA intrusion detection system evaluations as performed by Lincoln Laboratory. *ACM Trans. on Information Systems Security*, 3(4):262-294, 2000.

[30] M. Meier. A model for the semantics of attack signatures in misuse detection systems. In *Proc. ISC*, pages 158-169, 2004.

[31] H. D. Moore. The metasploit project—open-source platform for developing, testing, and using exploit code. http://www.metasploit.com, 2005.

[32] G. Nagy. Twenty years of document image analysis in PAMI. *IEEE Trans. Pattern Analysis and Machine Intelligence*, 22(1):36-62, 2000.

[33] V. Paxson. Bro: a system for detecting network intruders in realtime. In *Proc. USENIX*, pages 31-51, 1998.

[34] L. Portnoy, E. Eskin, and S. J. Stolfo. Intrusion detection with unlabeled data using clustering. In *Proc. ACM CSS Workshop on T Data Mining Applied to Security*, 2001.

[35] A. M. Robertson and P. Willett. Applications of n-grams in textual information systems. *Journal of Documentation*, 58(1):4869, 1998.

[36] M. Roesch. Snort: Lightweight intrusion detection for networks. In *Proc. LISA*, pages 229-238, 1999.

[37] S. Rubin, S. Jha, and B. P. Miller. Language-based generation and evaluation of NIDS signatures. In *Proc. IEEE Symposium on Security and Privacy*, pages 317, 2005.

[38] C. Shannon and D. Moore. The spread of the Witty worm. *Proc. IEEE Symposium on Security and Privacy*, 2(4):46-50, 2004.

[39] R. R. Sokal and P. H. Sneath. *Principles of numerical taxonomy*. Freeman, San Francisco, Calif., USA, 1963.

[40] C. Y. Suen. N-gram statistics for natural language understanding and text processing. *IEEE Trans. Pattern Analysis and Machine Intelligence*, 1(2):164-172, April 1979.

[41] K. Wang, G. Cretu, and S. J. Stolfo. Anomalous payload-based worm detection and signature generation. In *Proc. RAID*, 2005.

[42] K. Wang and S. J. Stolfo. Anomalous payload-based network intrusion detection. In *Proc. RAID*, pages 203-222, 2004.

[43] C. Warrender, S. Forrest, and B. Perlmutter. Detecting intrusions using system calls: alternative data methods. In *Proc. IEEE Symposium on Security and Privacy*, pages 133-145, 1999.

[44] C. Watkins. Dynamic alignment kernels. In A. J. Smola, P. L. Bartlett, B. Schölkopf, and D. Schuurmans, editors, *Advances in Large Margin Classifiers*, pages 39-50, Cambridge, MA, 2000. MIT Press.

A.

A.1. Anomaly Detectors

A.1.1. Global Anomaly Detectors

The simplified Mahalanobis distance [42] determines the center of mass of data µ and the variance of each dimension $\sigma_i$ in input space. The anomaly score is defined as the variance-scaled distance from x to µ:

$$m_{\mu,\sigma}(x) = \sum_{i=1}^{n} \frac{|x_i - \mu_i|}{\sigma_i}$$

The quarter-sphere SVM [17] is a kernel-based learning method that determines the center of mass of input data φ(µ) in a high-dimensional feature space using a non-linear mapping function φ: The anomaly score is defined as the distance from φ(x) to φ(µ) in feature space:

$$q_{\phi,\mu}(x) = \|\phi(x) - \phi(\mu)\|$$

A.1.2. Local Anomaly Detectors

Simplified single-linkage clustering [34] is a common clustering algorithm. Given a cluster assignment, the anomaly score is defined as the size of the cluster x: is assigned to:

$$s_c(x) = |c| \text{ for } x \in c$$

Our new method Zeta is an anomaly score based on the concept of k-nearest neighbors. The score is calculated as the mean distance of x to its k-nearest neighbors normalized by the mean inner-clique distance:

$$\zeta_k(x) = \frac{1}{k} \sum_{i=1}^{k} d(x, nn_i(x)) - \frac{1}{k^2} \sum_{i=1}^{k} \sum_{j=1}^{k} d(nn_i(x), nn_j(x))$$

A.2. Similarity Measures

A (dis)similarity measure is a binary function that maps x and y with component values $x_i$ and $y_i$ to a singular (dis) similarity score.

A.2.1. Metric Distances

The Canberra distance $d_c$ is a normalized form of the Manhattan distance. It expresses metric characteristics and distance scores lie within the range [0, 1]. The distance is suitable for histograms containing quantities and frequencies:

$$d_c(x, y) = \sum_{i=1}^{n} \frac{|x_i - y_i|}{x_i + y_i}$$

The "binarized" Manhattan distance $d_b$ is similar to the Hamming distance [13]. It is metric and maps the input vectors z and y to a binary space using the function b which returns 1 for non-zero values:

$$d_b(x, y) = \sum_{i=1}^{n} |b(x_i) - b(y_i)|$$

A.2-2. Similarity Coefficients

Similarity coefficients are often applied to binary data and express non-metric properties [2]. These coefficients are constructed over four summation variables a, b, c and d. The variable a defines the number of positive matching components (1-1), b the number of left mismatches (0-1), c the number of right mismatches (1-0) and d the number of negative matches (0-0).

The coefficients can be extended to non-binary data by modification of these summation variables. The degree of matching between two components can be defined as $\min(x_i, y_i)$ and accordingly mismatches as differences from $\min(x_i, y_i)$:

$$a = \sum_{i=1}^{n} \min(x_i, y_i),$$

$$b = \sum_{i=1}^{n} (x_i - \min(x_i, y_i)),$$

$$c = \sum_{i=1}^{n} (y_i - \min(x_i, y_i)).$$

The Czekanowski coefficient $s_c$ measures the ratio between positive matching components and the sum of all components [6]. In the extended form it can be expressed as following:

$$s_c(x, y) = \frac{2a}{2a + b + c} = \frac{2 \sum_{i=1}^{n} \min(x_i, y_i)}{\sum_{i=1}^{n} x_i + y_i}.$$

The second Kulczynski coefficient $s_k$ measures the ratio between positive matching components against the left- and right-hand side of mismatches [39]. In the extended form the second Kulczynski coefficient is defined as following:

$$s_k(x, y) = \frac{1}{2}\left(\frac{a}{a+b} + \frac{a}{a+c}\right)$$

$$= \frac{1}{2}\left(\frac{\sum_{i=1}^{n} \min(x_i, y_i)}{\sum_{i=1}^{n} x_i} + \frac{\sum_{i=1}^{n} \min(x_i, y_i)}{\sum_{i=1}^{n} y_i}\right).$$

Kernel functions as similarity measures for sequential data have been extensively studied in previous research. This contribution addresses the efficient computation of distance functions and similarity coefficients for sequential data. Two proposed algorithms utilize different data structures for efficient computation and yield a runtime linear in the sequence length. Experiments on network data for intrusion detection suggest the importance of distances and even non-metric similarity measures for sequential data.

1 Introduction

Sequences are a common non-vectorial data representation used in various machine learning and pattern recognition applications, e.g. textual documents in information retrieval, DNA sequences in bioinformatics or packet payloads in intrusion detection. An essential procedure for analysis of such data is the efficient computation of pairwise similarity between sequences.

Beside specialized string distances [e.g. 1, 2] a large class of similarity measures for sequential data can be defined over contained subsequences by embedding them in a high-dimensional feature space. Previous research focused on computation of kernel functions in such feature spaces. For example, the inner-product over n-gram or word frequencies has been widely used for analysis of textual documents [e.g. 3, 4, 5] or host-based intrusion detection [e.g. 6]. The challenge of uncovering information in DNA has influenced further advancement of kernel functions, e.g. by exploring different sets of subsequences [e.g. 7, 8, 9, 10] or incorporating mismatches, gaps and wildcards [e.g. 11, 12, 13].

There exist, however, a large amount of learning algorithms which are not directly suitable for kernel functions. In principle, any inner-product induces a Euclidean distance in feature space [14], yet the richness of content in sequential data and the variability of its characteristics in feature spaces motivate application of other distance functions.

A general technique for computation of similarity measures suitable for kernels, distances and similarity coefficients is proposed in this contribution. It is based on incremental accumulation of matches and mismatches between subsequences comprising a feature space. Two algorithms are presented that utilize different data structures for efficient computation: hash tables and tries. Both algorithms have linear runtime complexity in terms of sequence lengths.

The rest of the paper is organized as follows: Section 2 defines several similarity measures for sequential data including kernels, distances and similarity coefficients. Comparison algorithms and corresponding data structures are introduced in Section 3. Finally, experiments in Section 4 compare the efficiency of the introduced algorithms and illustrate their application in network intrusion detection.

2 Similarity Measures For Sequential Data

Given an alphabet $\Sigma$ of size N, a sequence x is defined as a concatenation of symbols from $\Sigma$. The content of a sequence can be modeled as a set of possibly overlapping subsequences w taken from a finite language $L \subset \Sigma^*$. We refer to these extracted subsequences as words. The language L constitutes the basis for calculating similarity of sequences and typically corresponds to a bag of characters, words or n-grams. Given a sequence z and a language L, an embedding into feature space is performed by calculating $\phi_w(x)$ for every w∈L appearing in x. Usually the function $\phi_w(x)$ returns the frequency of w in x, however, other definitions returning a count or a binary flag for w are possible. Furthermore we define l to be the length of x.

We assume that the total length of words in every sequence x is proportional to l. This assumption is valid, for example, for n-grams of fixed length n and non-overlapping words, and ensures linear runtime of the proposed algorithms. In context of kernels several approaches have been investigated that do not make such an assumption [e.g. 9, 10, 11, 12, 13], however, some of them come at a cost of super-linear complexity.

By utilizing the feature space induced through $\phi$, one can adapt classical kernel and distance functions to operate on sequences. Table 5 lists kernel functions and Table 6 distance functions that are implemented using the algorithms presented in Section 3.

Yet another way of measuring similarity are so called similarity coefficients [e.g. 15, 16]. They are non-metric and have been primarily used on binary data.

Similarity coefficients are constructed using three summation variables a, b and c. The variable a contains the number of positive matches (1-1), b the number of left mismatches (0-1) and c the number of right mismatches (1-0). The most common similarity coefficients are given in Table 7.

Similarity coefficients can be extended to non-binary data by modification of the summation variables. The degree of match for a word w∈L can be defined as $\min(\phi_w(x), \phi_w(y))$ and the respective mismatches are defined as deviations thereof:

$$a = \sum_{w \in L} \min(\phi_w(x), \phi_w(y))$$

$$b = \sum_{w \in L} [\phi_w(x) - \min(\phi_w(x), \phi_w(y))]$$

$$c = \sum_{w \in L} [\phi_w(y) - \min(\phi_w(x), \phi_w(y))]$$

3 Algorithms And Data Structures

In order to calculate the presented kernels, distances and similarity coefficients, one needs to establish a general model or similarity measures for sequential data. A key instrument for computation of kernel functions is finding words w ∈L present in two sequences x and y—we refer to these words as matches. For distances and similarity coefficients, we also need to consider words w ∈L present in x but not in y (and vice versa)—we refer to these words as mismatches[1].

[1] The term "mismatch" herein corresponds to two sequences being unequal and not, as often used in bioinformatics, to inexact matching of sequences.

Furthermore we introduce an outer function $\oplus$ which corresponds to the global aggregation performed in many similarity measures, e.g. the summation in various kernel and distance functions. Given these definitions, we can express a generic similarity measure s as $$s(x, y) = \bigoplus_{w \in L} m(x, y, w) \quad (1)$$

$$m(x, y, w) = \begin{cases} m^+(\phi_w(x), \phi_w(y)) & \text{if } w \text{ is a match} \\ m_x^-(\phi_w(x)) & \text{if } w \text{ is a mismatch in } x \\ m_y^-(\phi_w(y)) & \text{if } w \text{ is a mismatch in } y. \end{cases} \quad (2)$$

We can now reformulate the set of distances given in Table 6 using the functions $\oplus$, $m^+$, $m_x^-$ and $m_y^-$. The generalized formulations of some distances are presented in Table 8.

Adapting similarity coefficients to such a generic representation is even simpler, since only the three summation variables a, b and c need to be reformulated, as shown in Table 9.

3.1 Hash-Based Sequence Comparison

Figure 8:
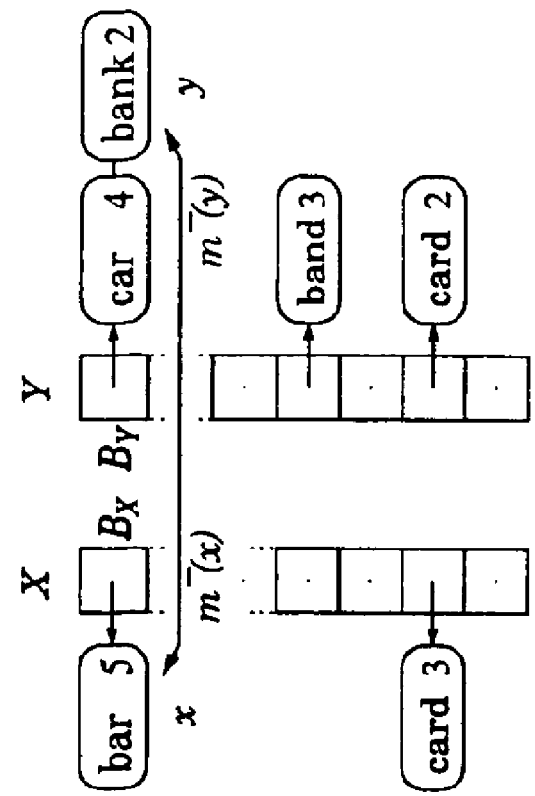
FIG. 8 shows hash table data structures and their comparison (b).
Figure 8:
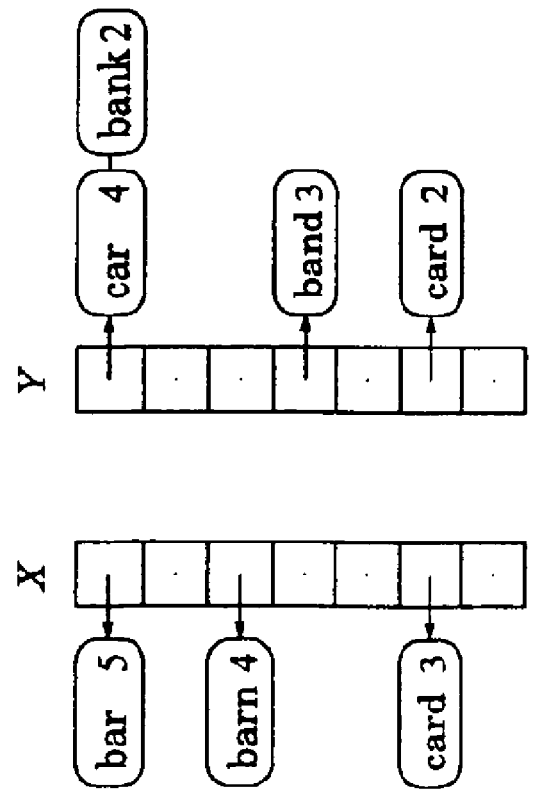

The classical scheme for computation of similarity measures over sequences utilizes indexed tables, or in the more general case hash tables [e.g. 4]. The words extracted from a sequence and corresponding frequencies or counts are stored in the bins of a hash table. FIG. 8(a) shows two hash tables carrying the words {"bar", "barn", "card"} and {"car", "bank", "band", "card"} with corresponding counts.

Algorithm 1 defines the comparison of two hash tables X and Y with fixed size M. The algorithm proceeds by looping over all M bins, checking for matching (c. Algorithm 1: Case 1) and mismatching words (cf. Algorithm 1: Case 2 & 3). FIG. 8(b) illustrates this process at the mismatches "bar" and "bank" which are stored in corresponding bins.

Algorithm 1. Hash-based Sequence Comparison

1: function COMPARE(X, Y)
2:     s ← 0
3:     for i ← 1, M do
4:        $B_X$ ← bins[X, i]
5:        $B_Y$ ← bins[Y, i]
6:        if $B_X$ ≠ NIL and $B_Y$ ≠ NIL then
7:           for all $x \in B_X$ and $y \in B_Y$ do
8:              if x = y then
9:                 $s \leftarrow s \oplus m^+(x, y)$   ▷ Case 1
10:            else
11:                $s \leftarrow s \oplus m^-(x) \oplus m^-(y)$   ▷ Case 2
12:        else if $B_X$ ≠ NIL then
13:           for all $x \in B_X$ do
14:              $s \leftarrow s \oplus m^-(x)$   ▷ Case 3
15:        else if $B_Y$ ≠ NIL then
16:           for all $y \in B_Y$ do
17:              $s \leftarrow s \oplus m^-(y)$   ▷ Case 3
18:     returns s Since the size of the hash tables is fixed at M, the average runtime for a comparison is θ(M). To avoid possible hash collisions, a high value of M>>l must be chosen in advance, otherwise the chaining of bins (Case 2) results in O(l$^2$) worst-case runtime for O(l) extracted words per sequence.

3.2 Trie-Based Sequence Comparison

Figure 9:
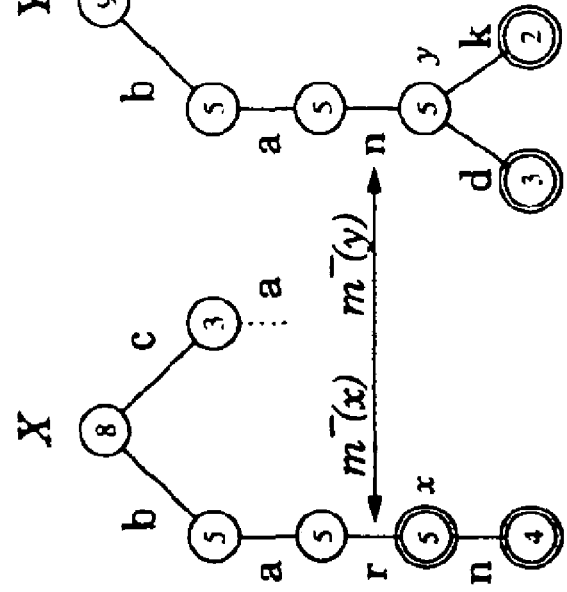
FIG. 9 shows trie data structure (a) and their comparison (b).
Figure 9:
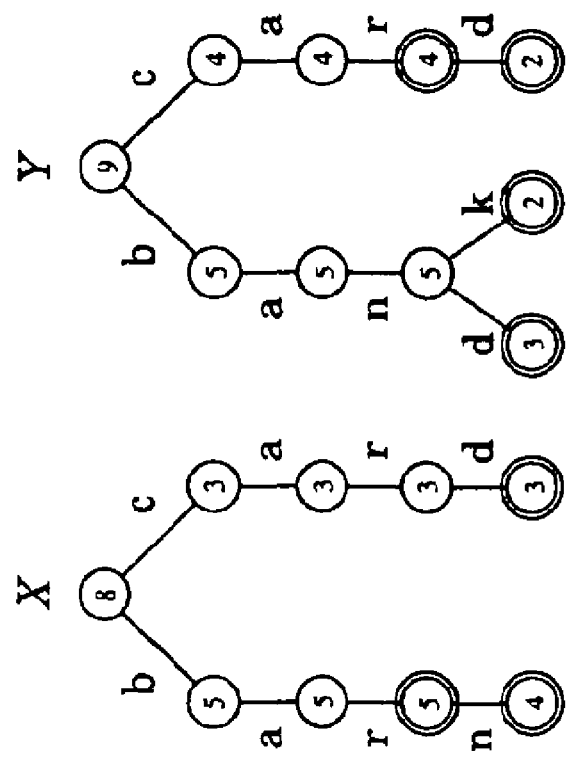

A trie is an N-ary tree, whose nodes are N-place vectors with components corresponding to the elements of Σ[17]. FIG. 9(a) shows two tries X and Y containing the same words as the hash tables in FIG. 8(a). The nodes of the tries are augmented to carry a variable reflecting the count of the passing sequence. The end of each extracted word is indicated by a marked circle. Application of tries to computation of kernel functions has been considered by [18].

Depending on the applied similarity measure the trie nodes can be extended to store other aggregated values which speed up calculations involving subtrees, e.g. for the Minkowski distance $\Sigma_w \phi_w(x)^k$ for all lower words w, Comparison of two tries can be carried out as in Algorithm 2: Starting at the root nodes, one traverses both tries in parallel, processing matching and mismatching nodes. If the traversal passes two equal and marked nodes, a matching word is discovered (Case 1), if only one node is marked a mismatch occurred (Case 2). The recursive traversal is stopped if two nodes do not match, and thus two sets of underlying mismatching words are discovered (Case 3). FIG. 9(b) shows a snapshot of such a traversal. The nodes x and y are not equal, and the words ("bar", "barn") and ("band", "bank") constitute mismatches.

As an invariant, the nodes under consideration in both tries remain at the same depth and thus the worst-case runtime is O(1). An advantage of the trie data structure comes into play especially if the provided alphabet is large and a lot of mismatches occur. The traversal discovers mismatching words after passing the first few symbols and omits further unnecessary comparisons.

Algorithm 2. *Trie*-based Sequence Comparison

```
1:  function COMPARE(X, Y)
2:      s ← 0
3:      for i ← 1, N do
4:          x ← child[X, i]
5:          y ← child[Y, i]
6:          if x ≠ NIL and y ≠ NIL then
7:              if end[x] and end[y] then
8:                  s ← s ⊕ m⁺(x, y)              ▷ Case 1
9:              else if end[x] then
10:                 s ← s ⊕ m⁻(x)                 ▷ Case 2
11:             else if end[y] then
12:                 s ← s ⊕ m⁻(y)                 ▷ Case 2
13:             s ← s ⊕ COMPARE(x, y)
14:         else
15:             if x ≠ NIL then
16:                 s ← s ⊕ m⁻(x)                 ▷ Case 3
17:             if y ≠ NIL then
18:                 s ← s ⊕ m⁻(y)                 ▷ Case 3
19:     return s
```

4 Experimental Results
4.1 Efficiency of Data Structures

Efficiency of the two proposed algorithms has been evaluated on four benchmark data sets for sequential data: DNA sequences of the human genome [19], system call traces and connection payloads from the DARPA 1999 data set [20] and news articles from the Reuters-21578 data set [21]. Table 10 gives an overview of the data sets and their specific properties.

For each data set 100 sequences were randomly drawn and n-grams of lengths 3, 5 and 7 extracted. The n-grams of each sequence were stored in tries and hash tables with varying size from $10^2$ to $10^6$. Subsequently the Canberra distance was calculated pairwise over the tries and hash tables using the proposed algorithms, resulting in 5000 comparison operations per setup. The procedure was repeated 10 times and the runtime was averaged over all runs. The experimental results are given in Table 11.

The average runtime of the hash-based algorithm strongly depends on the size of the hash table. The optimal value varies for different data sets and values of n. However, in 10 of 12 cases the trie-based algorithm performs equally well or better than the best hash table setup, being independent of a parameter.

4.2 Application: Network Intrusion Detection

To demonstrate the proposed algorithms on realistic data, we conducted an experiment for unsupervised learning in network intrusion detection. The underlying network data was generated by the members of our laboratory using virtual network servers. Recent network attacks were injected by a penetration-testing expert.

Figure 10:
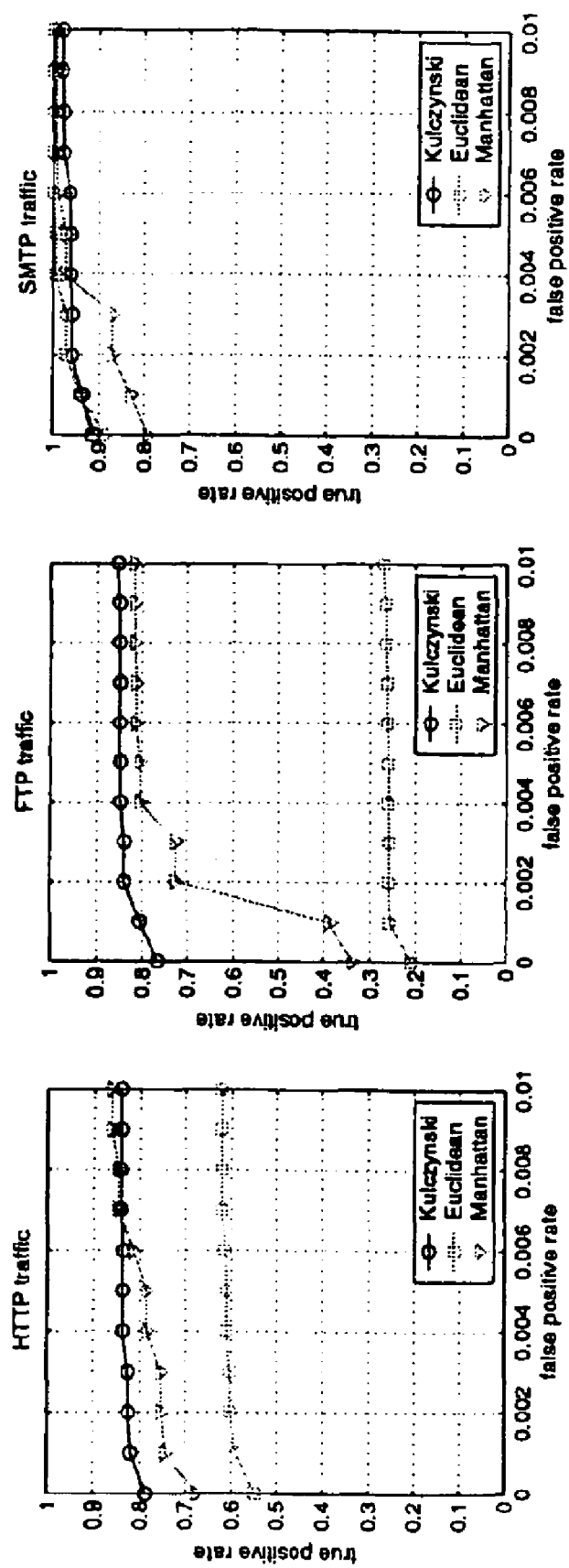
FIG. 10 shows detection performance for network detection.

A distance-based anomaly detection method [22] was applied on 5-grams extracted from byte sequences of TCP connections using different similarity measures: a linear kernel (Euclidean distance), the Manhattan distance and the Kulczynski coefficient. Results for the common network protocols HTTP, FTP and SMTP are given in FIG. 10.

Application of the Kulczynski coefficient yields the highest detection accuracy. Over 78% of attacks for each protocol are identified with no false-positives. In comparison the Euclidean distances fails to uncover good geometric properties for discrimination of attacks in this particular setup.

5 Conclusions

We have shown that, similarly to kernels, a large number of distances and similarity coefficients can be efficiently computed for sequential data. The use of such similarity measures allows one to investigate unusual metrics for application of machine learning in specialized problem domains. As an example, the best results in our experiments on unsupervised learning for network intrusion detection have been obtained with the Kulczynski coefficient over n-grams of connection payloads. Thus direct application of distances over sequential data may be favorable over implicit use of the Euclidean distance induced by kernels. Especially promising are further applications of the proposed algorithms in computer security and bioinformatics.

REFERENCES

[1] Hamming, R. W.: Error-detecting and error-correcting codes. Bell System Technical Journal 29(2) (1950) 147-160

[2] Levenshtein, V. I.: Binary codes capable of correcting deletions, Insertions, and reversals. Doklady Akademii Nauk SSSR 163(4) (1964) 845448

[3] Salton, G.: Mathematics and information retrieval. Journal of Documentation 35(1) (1979) 1-29

[4] Damashek, M.: Gauging similarity with n-grams: Language-independent categorization of text. Science 267(5199) (1995) 843-848

[5] Joachims, T.: Text categorization with support vector machines: Learning with many relevant features. Technical Report 23, LS VIII, University of Dortmund (1997)

[6] Eskin, E., Arnold, A., Prerau, M., Portnoy, L., Stolfo, S.: A geometric framework for unsupervised anomaly detection: detecting intrusions in unlabeled data. In: Applications of Data Mining in Computer Security. Kluwer (2002)

[7] Zien, A., Rätsch, C., Mika, S., Schölkopf, B., Lengauer, T., Müller, K. R.: Engineering Support Vector Machine Kernels That Recognize Translation Initiation Sites. BioInformatics 16(9) (2000) 799-807
[8] Leslie, C., Eskin, E, Noble, W.: The spectrum kernel: A string kernel for SVM protein classification. In: Proc. Pacific Symp. Biocomputing. (2002) 564-575
[9] Lodhi, H., Saunders, C., Shawe-Taylor, J., Cristianini, N., Watkins, C.: Text classification using string kernels. Journal of Machine Learning Research 2 (2002) 419-444
[10] Vishwanathan, S., Smola, A.: Fast Kernels for String and Tree Matching. In: Kernels and Bioinformatics. MIT Press (2004) 113-130
[11] Leslie, C., Eskin, E., Cohen, A., Weston, J., Noble, W.: Mismatch string kernel for discriminative protein classification. Bioinformatics 1(1) (2003) 1-10
[12] Leslie, C., Kuang, R.: Fast string kernels using inexact matching for protein sequences. Journal of Machine Learning Research 5 (2004) 1435-1455
[13] Rousu, J., Shawe-Taylor, J.: Efficient computation of gapped substring kernels for large alphabets. Journal of Machine Learning Research 6 (2005) 1323-1344
[14] Schölkopf, B.: The kernel trick for distances. In Leen, T., Diettrich, T., Tresp, V., eds.: Advances in Neural Information Processing Systems 13, NUT Press (2001)
[15] Jaccard, P.: Contribution au problems de l'immigration post-glaciaire de la flore alpine. Bulletin de la Société Vaudoise des Sciences Naturelles 36 (1900) 87-130
[16] Anderberg, M.: Cluster Analysis for Applications. Academic Press, Inc., New York, N.Y., USA (1973)
[17] Knuth, D.: The art of computer programming. Volume 3. Addison-Wesley (1973)
[18] Shawe-Taylor, J., Cristianini, N.: Kernel methods for pattern analysis. Cambridge University Press (2004)
[19] Sonnenburg, S., Zien, A., Rätsch, C.: ARTS: Accurate recognition of transcription starts in human. Bioinformatics (2006) submitted.
[20] Lippmann, R., Haines, J., Pried, D., Korba, J., Das, K.: The 1999 DARPA off-line intrusion detection evaluation. Computer Networks 34(4) (2000) 579-595
[21] Lewis, D. D.: Reuters-21578 text categorization test collection. AT&T Labs Research (1997)
[22] Rieck, K., Laskov, P.: Detecting unknown network attacks using language models. In: Proc. DIMVA. (2006) to appear.

We propose a generic algorithm for computation of similarity measures for sequential data. The algorithm uses generalized suffix trees for efficient calculation of various kernel, distance and non-metric similarity functions. Its worst-case run-time is linear in the length of sequences and independent of the underlying embedding language, which can cover words, k-grams or all contained subsequences. Experiments with network intrusion detection. DNA analysis and text processing applications demonstrate the utility of distances and similarity coefficients for sequences as alternatives to classical kernel functions.

1 Introduction

The ability to operate on sequential data is a vital prerequisite for application of machine learning techniques in many challenging domains. Examples of such applications are natural language processing (text documents), bioinformatics (DNA and protein sequences) and computer security (byte streams or system call traces). A key instrument for handling such data is the efficient computation of pairwise similarity between sequences. Similarity measures can be seen as an abstraction between particular structure of data and learning theory.

One of the most successful similarity measures thoroughly studied in recent years is the kernel function [e.g. 1-3]. Various kernels have been developed for sequential data, starting from the original ideas of Watkins [4] and Haussler [5] and extending to application-specific kernels such as the ones for text and natural language processing [e.g. 6-8], bioinformatics [e.g. 9-14], spam filtering [15] and computer security [e.g. 16; 17].

Although kernel-based learning has gained a major focus in machine learning research, a kernel function is obviously only one of various possibilities for measuring similarity between objects. The choice of a similarity measure is essentially determined by (a) understanding of a problem and (b) properties of the learning algorithm to be applied. Some algorithms operate in vector spaces, others in inner product, metric or even non-metric feature-spaces. Investigation of techniques for learning in spaces other than RKHS is currently one of the active research fields in machine learning [e.g. 18-21].

The focus of this contribution lies on general similarity measures for sequential data, especially on efficient algorithms for their computation. A large number of such similarity measures can be expressed in a generic form so that a simple linear-time algorithm can be applied for computation of a wide class of similarity measures. This algorithm enables the investigation of alternative representations of problem domain knowledge other than kernel functions. As an example, two applications are presented for which replacement of a kernel—or equivalently, the Euclidean distance—with a different similarity measure yields a significant improvement of accuracy in an unsupervised learning scenario.

The rest of the paper is organized as follows. Section 2 provides a brief review of common similarity measures for sequential data and introduces a generic form in which a large variety of them can be cast. The generalized suffix tree and a corresponding algorithm for linear-time computation of similarity measures are presented in Section 3. Finally, the experiments in Section 4 demonstrate efficiency and utility of the proposed algorithm on real-world applications: network intrusion detection. DNA sequence analysis and text processing.

2 Similarity Measures For Sequences 2.1 Embedding of sequences

A common way to define similarity measures for sequential data is via explicit embedding into a high-dimensional feature space. A sequence x is defined as concatenation of symbols from a finite alphabet $\Sigma$. To model the content of a sequence, we consider a language $L \subseteq \Sigma^*$ comprising subsequences $w \in L$. We refer to these subsequences as words, even though they may not correspond to a natural language. Typical examples for L are a "bag of words" [e.g. 22], the set of all sequences of fixed length (k-grams or k-mers) [e.g. 10; 23] or the set of all contained subsequences [e.g. 8; 24].

Given a language L, a sequence x can be mapped into an |L|-dimensional feature space by calculating an embedding function $\phi_w(x)$ for every $w \in L$ appearing in x. The function $\phi_w$ is defined as follows $$\phi_w: \Sigma^* \to R^+ \cup \{0\}, \phi_w(x) := \psi(occ(w,x)) \cdot W_w \quad (1)$$

where occ(w,x) is the number of occurrences of w in x, $\psi$ a numerical transformation, e.g. a conversion to frequencies, and W a weighting assigned to individual words, e.g. length-dependent or frequency-dependent (TFIDF) weights [cf. 3; 24]. By employing the feature space induced through L and $\phi$, one can adapt many vectorial similarity measures to operate on sequences.

The feature space defined via explicit embedding is sparse, since the number of non-zero dimensions for each feature vector is bounded by the sequence length. Thus the essential parameter for measuring complexity of computation is the sequence length, denoted hereinafter as n. Furthermore, the length of a word |w| or in case of a set of words the maximum length is denoted by k.

2.2 Vectorial Similarity Measures

Several vectorial kernel and distance functions can be applied to the proposed embedding of sequential data. A list of common functions in terms of L and φ is given in Table 12.

Beside kernel and distance functions, a set of rather exotic similarity coefficients is also suitable for application to sequential data [25]. The coefficients are constructed using three summation variables a, b and c, which in the case of binary vectors correspond to the number of matching component pairs (1-1), left mismatching pairs (0-1) and right mismatching pairs (1-0) [cf. 26; 27] Common similarity coefficients are given in Table 13. For application to non-binary data these summation variables can be extended as proposed in [25]:

$$a = \sum_{w \in L} \min(\phi_w(x), \phi_w(y))$$

$$b = \sum_{w \in L} [\phi_w(x) - \min(\phi_w(x), \phi_w(y))]$$

$$c = \sum_{w \in L} [\phi_w(y) - \min(\phi_w(x), \phi_w(y))]$$

2.3 A Generic Representation

One can easily see that the presented similarity measures can be cast in a generic form that consists of an outer function $\oplus$ and an inner function m:

$$s(x, y) = \bigoplus_{w \in L} m(\phi_w(x), \phi_w(y)) \quad (2)$$

Given this definition, the kernel and distance functions presented in Table 1 can be re-formulated in terms of $\oplus$ and m. Adaptation of similarity coefficients to the generic form (2) involves a reformulation of the summation variables a, b and c. The particular definitions of outer and inner functions for the presented similarity measures are given in Table 14. The polynomial and RBF kernels are not shown since they can be expressed in terms of a linear kernel or a distance respectively.

3 Generalized Suffix Trees For Comparison Of Sequences

The key to efficient comparison of two sequences lies in considering only the minimum of words necessary for computation of the generic form (2) of similarity measures. In the case of kernels only the intersection of words in both sequences needs w be considered, while the union of words is needed for calculating distances and non-metric similarity coefficients. A simple and well-known approach for such comparison is representing the words of each sequence in a sorted list. For words of maximum length k such a list can be constructed in O(kn log n) using general sorting or O(kn) using radix-sort. If the length of words k is unbounded, sorted lists are no longer an option as the sorting time becomes quadratic.

Thus, special data structures are needed for efficient comparison of sequences. Two data structures previously used for computation of kernels are tries [28; 29] and suffix trees [30]. Both have been applied for computation of a variety of kernel functions in O(kn) [3, 10] and also in O(n) run-time using matching statistics [24]. In this contribution we will argue that a generalized suffix tree is suitable for computation of all similarity measures of the form (2) in O(n) run-time.

Figure 11:
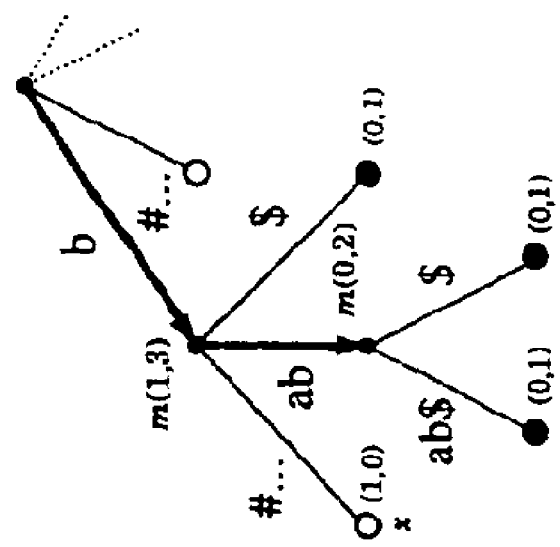
FIG. 11 shows a generalized suffix tree for "aab#" and "babab$" (a) and a snapshot of its traversal (b).
Figure 11:
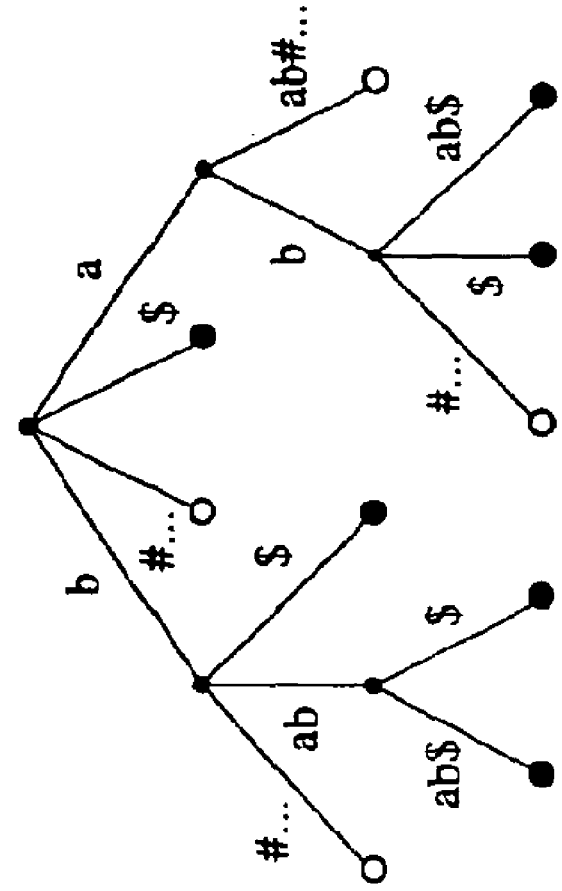

A generalized suffix tree (GST) is a tree containing all suffixes of a set of strings $x_1, \ldots, x_i$ [31]. The simplest way to construct a generalized suffix tree is to extend each string $x_i$ with a delimiter $\$_i$ and to apply a suffix tree construction algorithm [e.g. 32] to the concatenation of strings $x_1\$_1 \ldots x_l\$_l$. In the remaining part we will restrict ourselves to the case of two strings x and y delimited by # and \$, computation of an entire similarity matrix using a single GST for a set of strings being a straightforward extension. An example of a generalized suffix tree for the strings "aab#" and "babab\$" is shown in FIG. 11(a).

Once a generalized suffix tree is constructed, it remains to determine the number of occurrences occ(w, x) and occ(w, y) of each word w present in the sequences x and y. Unlike the case for kernels for which only nodes corresponding to both sequences need to be considered [24], the contributions must be correctly computed for all nodes in the generalized suffix tree. The following simple recursive algorithm computes a generic similarity measure between the sequence x and y in one depth-first traversal of the generalized suffix tree (cf. Algorithm 1).

The algorithm exploits the fact that a leaf in a GST representing a suffix of x contributes exactly 1 to occ(w, x) if w is the prefix of this suffix—and similarly for y and occ(w, y). As the GST contains all suffixes of x and y, every word w in x and y is represented by at least one leaf. Whether a leaf contributes to x or y can be determined by considering the edge at the leaf. Due to the uniqueness of the delimiter #, no branching nodes can occur below an edge containing #, thus a leaf node at an edge starting before the index of # must contain a suffix of x; otherwise it contains a suffix of y. The contributions of all leaves are aggregated in two variables z and y during a post-order traversal. At each node the inner function m of (2) is calculated using ψ(x) and ψ(y) according to the embedding φ in (1). A snapshot of the traversal procedure is illustrated in FIG. 11(b).

To account implicit nodes along the edges of the GST and to support weighted embeddings φ, the weighting function WEIGHT introduced in [24] is employed. At a node υ the function takes the beginning (begin|υ|) and the end (end|υ|) of the incoming edge and the depth of node (depth|υ|) as arguments to determine how much the node and edge contribute to the similarity measure, e.g. for k-gram models only nodes up to a path depth of k need to be considered.

Algorithm 1 Suffix tree comparison

1: function COMPARE(x, y)

2:     S ← SUFFIX TREE(x ≠ y S)

3:     (x, y, s) ← MATCH(root[S])

```
 4:     return s
 5:
 6: function MATCH(v)
 7:     if v is leaf then
 8:         s ← 0
 9:         if begin[v] ≤ index_# then
10:             (x, y) ← (1, 0)         ▷ Leaf of a suffix of x
11:             j ← index_# − 1
12:         else
13:             (x, y) ← (0, 1)         ▷ Leaf of a suffix of y
14:             j ← index_# − 1
15:     else
16:         (x, y, s) ← (0, 0, 0)
17:         for all c in children[v] do
18:             (x̂, ŷ, ŝ) ← MATCH(c)    ▷ Traverse GST
19:             (x, y, s) ← (x + x̂, y + ŷ, s ⊕ ŝ)
20:         j ← end[v]
21:     W ← WEIGHT(begin[v], j, depth[v])
22:     s ← s ⊕ m(ψ(x)W, ψ(y)W)          ▷ Cf. definitions in (1) and (2)
23:     return(x, y, s)
```

Similarly to the extension of string kernels proposed in [33], the GST traversal can be performed on an enhanced suffix array [34] for further run-time and space reduction.

To prove correctness of our algorithm, a different approach must be taken than the one in [24]. We cannot claim that the computed similarity value is equivalent to the one returned by the matching statistic algorithm, since the latter is restricted to kernel functions. Instead we show that at each recursive call to the MATCH function correct numbers of occurrences are maintained.

Theorem 1. A word w occurs occ(wn, x) and occ(w, y) times in x and y if and only if MATCH(w̄) returns x=occ(w, x) and y=occ(w, y), where w̄ is the node at the end of a path from the root reassembling w in the generalized suffix tree of x and y.

Proof. If w occurs m times in x, there exist exactly m suffixes of x with w as prefix. Since w corresponds to a path from the toot of the GST to a node w̄ all m suffixes must pass w̄. Due to the unique delimiters # each suffix of x corresponds to one leaf node in the GST whose incoming edge contains #. Hence m equals occ(w, x) and is exactly the aggregated quantity z returned by MATCH(w̄). Likewise, occ(w, y) is the number of suffixes beginning after # and having a prefix w. which is computed by y.

4 Experimental Results
4.1 Run-Time Experiments

In order to illustrate the efficiency of the proposed algorithm, we conducted run-time experiments on three benchmark data sets for sequential data: network connection payloads from the DARPA 1999 IDS evaluation [35], news articles from the Reuters-21579 data set [36] and DNA sequences from the human genome [14]. Table 15 gives an overview of the data sets and their specific properties. We compared the run-time of the generalized suffix tree algorithm with a recent trie-based method supporting computation of distances. Tries yield better or equal run-time complexity for computation of similarity measures over k-grams than algorithms using indexed arrays and hash tables. A detailed description of the trie-based approach is given in [25]. Note that in all of the following experiments tries were generated in a pre-processing step and the reported run-time corresponds to the comparison procedure only.

Figure 12:
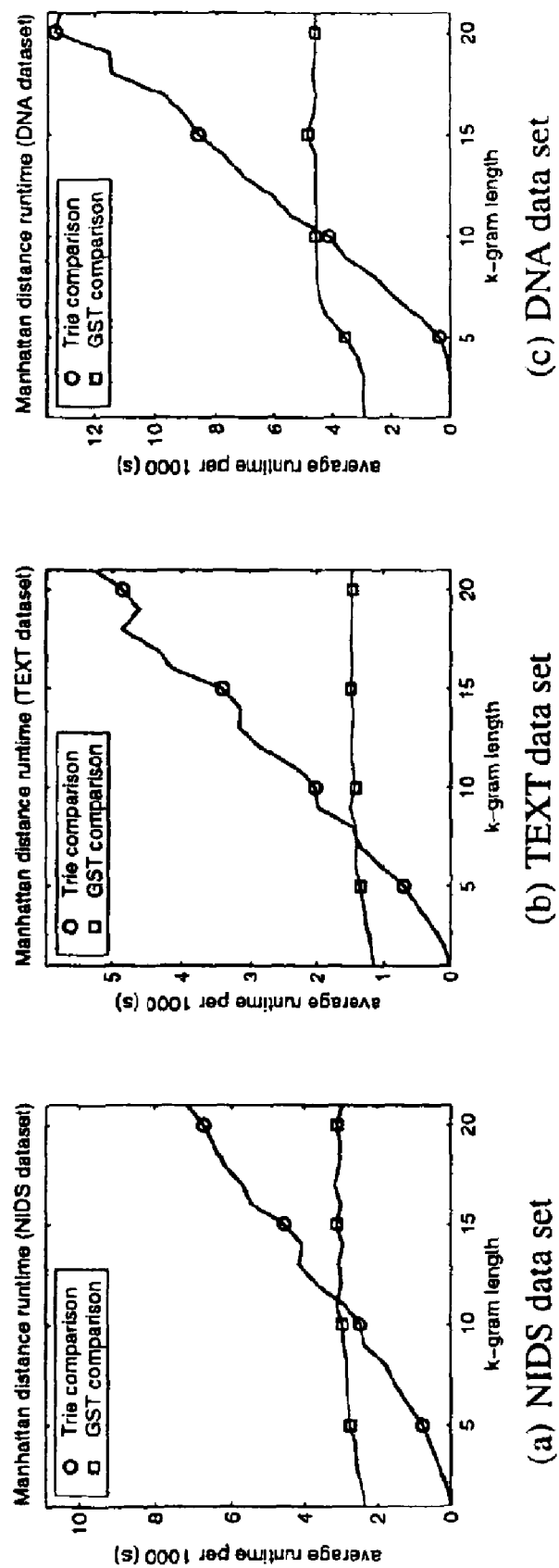
FIG. 12 shows run-time performance for varying k-gram lengths of a NIDS data set (a), a TEXT data set (b), and a DNA data set (c).

For each of the three data sets, we implemented the following experimental protocol: the Manhauan distances were calculated for 1000 pairs of randomly selected sequences using k-grams as an embedding language. The procedure was repeated 10 times for various values of k, and the run-lime was averaged over all runs. FIG. 12 compares the run-time of sequence comparison algorithms using the generalized suffix trees and tries. On all three data sets the trie-based comparison has a low run-time for small values of n but grows linearly with k. The algorithm using a generalized suffix tree is independent from complexity of the embedding language, although this comes at a price of higher constants due to a more complex data structure. It is obvious that a generalized suffix tree is the algorithm of choice for higher values of k.

4.2 Applications

As a second part of our evaluation, we show that generality of our approach allowing to compute diverse similarity measures pays off when it comes to real applications, especially in an unsupervised learning scenario. The experiments were performed for (a) intrusion detection in real network traffic and (b) transcription start site (TSS) recognition in DNA sequences.

Figure 13:
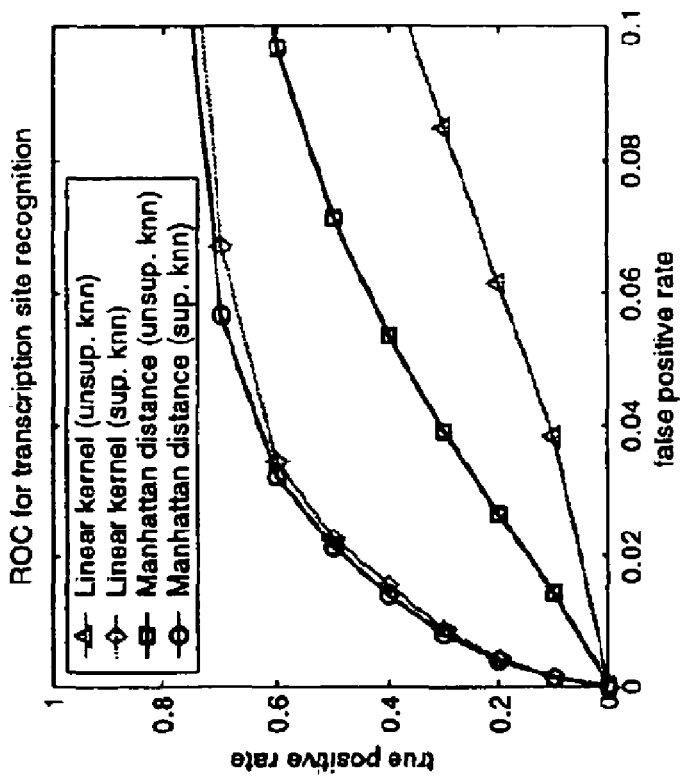
FIG. 13 shows comparison of similarity measures on the network (a) and DNA data (b).
Figure 13:
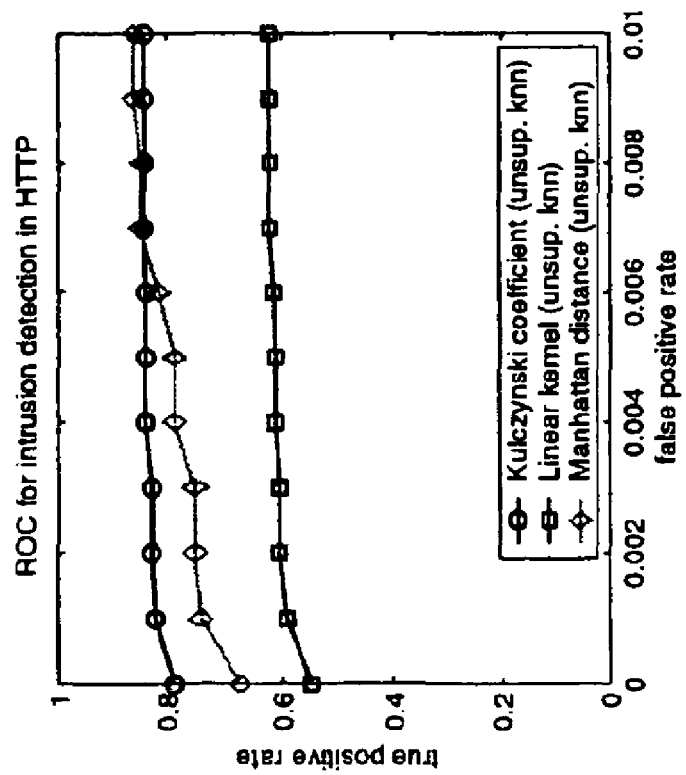

For the first application, network data was generated by members of our laboratory using virtual network servers. Recent attacks were injected by a penetration-testing expert. The distance-based anomaly detection method Zeta [17] was applied to 5-grams extracted from byte sequences of TCP connections using different similarity measures: then linear kernel, the Manhattan distance and the Kulczynski coefficient The results on network data from the HTTP protocol are shown in FIG. 13(a). Application of the Kulczynski coefficient yields the highest detection accuracy. Over 78% of all attacks are identified with no false-positives in an unsupervised setup. In comparison, the linear kernel yields roughly 30% lower detection rates.

The second application focused on TSS recognition in DNA sequences. The data set comprises fixed length DNA sequences that either cover the TSS of protein coding genes or have been extracted randomly from the interior of genes [14]. We evaluated three methods on this data: an unsupervised k-nearest neighbor (kNN) classifier, a supervised and bagged kNN classifier and a Support Vector Machine (SVM). Each method was trained and tested using a linear kernel and the Manhattan distance as a similarity measure over 4-grams. FIG. 13(b) shows the performance achieved by the unsupervised and supervised versions of the kNN classifier[1]. Even though the linear kernel and the Manhattan distance yield similar accuracy in a supervised setup, their performance differs significantly in unsupervised application. In the absence of prior knowledge of labels the Manhattan distance expresses better discriminative properties for TSS recognition than the linear kernel. For the supervised application the classification performance is bounded for both similarity measures, since only some discriminative features for TSS recognition are encapsulated in n-gram models [14].

[1] Results for the SVM are similar to the supervised kNN and have been omitted.

5 Conclusions

Kernel functions for sequences have recently gained strong attention in many applications of machine learning, especially in bioinformatics and natural language processing. In this contribution we have shown that other similarity measures such as metric distances or non-metric similarity coefficients can be computed with the same run-time complexity as kernel functions. The proposed algorithm is based on a post-order traversal of a generalized suffix tree of two or more sequences. During the traversal, the counts of matching and mismatching words from an embedding language are computed in time linear in sequence length—regardless of the particular kind of chosen language: words, k-grams or even all consecutive subsequences. By using a generic representation of the considered similarity measures based on an outer and inner function, the same algorithm can be applied for various kernel, distance and similarity functions on sequential data.

Our experiments demonstrate that the use of general similarity measures can bring significant improvement to learning accuracy—in our case observed for unsupervised learning— and emphasize importance of further investigation of distance- and similarity-based teaming algorithms.

Acknowledgments

The authors gratefully acknowledge the funding from Bundesministerium Forschung under the project MIND (FKZ 01-SC40A) and would like to thank KI; and Mikio Braun for fruitful discussions and support.

REFERENCES

[1] V. N. Vapnik. Statistical Learning Theory. Wiley, New York. 1998.
[2] B. Schölkopf and A. J. Smola. *Learning with Kernels*. MIT Press, Cambridge, Mass., 2002.
[3] J. Shawe-Taylor and N. Cristianini. *Kernel methods for pattern analysis*. Cambridge University Press, 2004.
[4] C. Watkins. Dynamic alignment kernels. In A. J. Smola, P. L. Bartlett, B. Schölkopf, and D. Schuurmans, editors. *Advances in Large Margin Classifier*, pages 39-50, Cambridge, Mass., 2000. MIT Press.
[5] D. Haussler. Convolution kernels on discrete structures. Technical Report UCSC-CRL-99-10, UC Santa Cruz, July 1999.
[6] T. Joachims. Text categorization with support vector machines: Learning with many relevant features. Technical Report 23, LS VIII, University of Dortmund, 1997.
[7] E. Leopold and J. Kindermann. Text categorization with Support Vector Machines how to represent texts in input space? *Machine Learning*. 46:423-444, 2002.
[8] H. Lodhi, C. Saunders. J. Shawe-Taylor, N. Cristianini, and C. Watkins. Text classification using string kernels. *Journal of Machine Learning Research*, 2:419-444, 2002.
[9] A. Zien, G. Rätsch, S. Mika B. Schölkopf, T. Lengauer, and K.-R. Müller. Engineering Support Vector Machine Kernels That Recognize Translation Initiation Sites. *Bioinformatics*, 16(9):799-807, September 2000.
[10] C. Leslie, E. Eskin, and W. S. Noble. The spectrum kernel: A string kernel for SVM protein classification. In *Proc. Pacific Symp. Biocomputing*. pages 564-575, 2002.
[11] C. Leslie, E. Eskin, A. Cohen, J. Weston, and W. S. Noble. Mismatch string kernel for discriminative protein classification. *Bioinformatics*, 1(1):1-10, 2003.
[12] J. Rousu and J. Shawe-Taylor. Efficient computation of gapped substring kernels for large alphabets. *Journal of Machine Learning Research*, 6:1323-1344, 2005.
[13] G. Rätsch, S. Sonnenburg, and B. Schölkopf. RASE: recognition of alternatively spliced exons in C. elegans. *Bioinformatics*. 21:i369-i377, June 2005.
[14] S. Sonnenburg. A. Zien, and G. Rätsch. ARTS: Accurate Recognition of Transcription Starts in Human. *Bioinformatics*, 22(14):e472-e480, 2006.
[15] H. Drucker. D. Wu. and V. N. Vapnik Support vector machines for spam categorization. *IEEE Transactions on Neural Networks*, 10(5):1048-1054, 1999.
[16] E Eskin. A. Arnold, M. Prerau. L. Portnoy. and S. Stolfo. *Applications of Data Mining in Computer Security*. chapter A geometric framework for unsupervised anomaly detection: detecting intrusions in unlabeled data. Kluwer, 2002.
[17] K. Rieck and P. Laskov. Detecting unknown network attacks using language models. In *Proc. DIMVA*, pages 74-90, July 2006.
[18] T. Graepel. R. Herbrich. P. Bollmann-Sdorra. and K. Obermayer. Classification on pairwise proximity data. In M. S. Kearns. S. A. Solla, and D. A. Cohn. editors, *Advances in Neural Information Processing Systems*. volume II, pages 438-444. MIT Press, 1999.
[19] V. Roth. J Laub, M. Kawanabe, and J. M. Buhmann. Optimal cluster preserving embedding of non-metric proximity data. *IEEE Trans. PAMI*, 25:1540-1551, December 2003.
[20] J. Laub and K.-R. Müller. Feature discovery in non-metric pairwise data. *Journal of Machine Learning*, 5(July):801-818, July 2004.
[21] C. Ong. X. Mary. S. Canu. and A. J. Smola. Learning with non-positive kernels. In *Proc. ICML*, pages 639-646, 2004.
[22] C. Salton. Mathematics and information retrieval. *Journal of Documentation*, 35(1):1-29, 1979.
[23] M. Damashek. Gauging similarity with n-grams: Language-independent categorization of text. *Science*. 267(5199):43-848, 1995.

[24] S. V. N. Vishwanathan and A. J. Smola. *Kernels and Bioinformatics*, chapter Fast Kernels for String and Tree Matching, pages 13-130. MIT Press, 2004.

[25] K. Rieck, P. Laskov, and K.-R. Müller. Efficient algorithms for similarity measures over sequential data: A look beyond kernels. In *Proc. DAGM*, pages 374-383, September 2006.

[26] R. R. Sokal and P. H. Sneath. *Principles of numerical taxonomy*. Freeman, San Francisco, Calif., USA. 1963.

[27] M. R. Anderberg. *Cluster Analysis for Applications*. Academic Press, Inc., New York, N.Y., USA, 1973.

[28] E. Fredkin. Trie memory. *Communications of ACM*, 3(9):490-499, 1960.

[29] D. Knuth. *The art of computer programming*, volume 3. Addison-Wesley. 1973.

[30] P. Weiner. Linear pattern matching algorithms. In *Proc. 14th Annual Symposium on Switching and Automata Theory*, pages 1-11, 1973.

[31] D. Gusfield. *Algorithms on strings, trees, and sequences*. Cambridge University Press, 1997.

[32] E. Ukkonen. Online construction of suffix tree. *Algorithmica*, 14(3):249-260, 1995.

[33] C. H. Teo and S. V. N. Vishwanathan. Fast and space efficient string kernels using suffix arrays. In *Proceedings, 23rd ICMP*, pages 939-936. ACM Press, 2006.

[34] M. I. Abouelhoda. S. Kurtz, and E. Ohlebusch. Replacing suffix trees with enhanced suffix arrays. *Journal of Discrete Algorithms*, 2(1):53-86, 2002.

[35] R. Lippmann, J. W. Haines, D. J. Fried, J. Korba, and K. Das. The 1999 DARPA off-line intrusion detection evaluation. *Computer Networks*, 34(4):579-595, 2000.

[36] D. D. Lewis. Reuters-21578 text categorization test collection. AT&T Labs Research, 1997.

TABLE 1

| HTTP attacks | FTP attacks | SMTP attacks |
| --- | --- | --- |
| HTTP tunnel | .rhost upload | Sendmail exploit |
| PHF CGI attack | NcFTP exploit | Mail: Spoofed frame |
|  | Password guessing | Mail: PowerPoint macro |
|  |  | Mail: SSH trojan horse |

TABLE 2

| HTTP attacks | FTP attacks | SMTP attacks |
| --- | --- | --- |
| HTTP tunnel | 3COM 3C exploit | CMAIL Server 2.3 exploit |
| IIS 4.0 htr exploit | GlobalScape 3.x exploit | dSMTP 3.1b exploit |
| IIS 5.0 printer exploit | Nessus FTP scan | MS Exchange 2000 exploit |
| IIS unicode attack | ProFTPd 1.2.7. exploit | MailCarrier 2.51 exploit |
| IIS 5.0 webdav exploit | Serv-U FTP exploit | Mail-Max SMTP exploit |
| IIS w3who exploit | SlimFTPd 3.16 exploit | Nessus SMTP scan |
| Nessus HTTP scan | WarFTPd 1.65 pass exploit | NetcPlus SmartServer3 exploit |
| PHP script attack | WarFTPd 1.65 user exploit | Personal Mail 3.072 exploit |
|  | WsFTPd 5.03 exploit | Sendmail 8.11.6 exploit |
|  | WU-FTPd 2.6.1 exploit |  |

TABLE 3

| Similarity measure | Anomaly detector | AUC |
| --- | --- | --- |
| HTTP protocol | | |
| Kulczynski coefficient | Zeta | 0.9304 |
| Kulczynski coefficient | Quarter-sphere SVM | 0.9253 |
| Czekanowski coefficient | Zeta | 0.9219 |
| FTP protocol | | |
| Kulczynski coefficient | Zeta | 0.9276 |
| Czekanowski coefficient | Single-linkage clustering | 0.8609 |
| Kulczynski coefficient | Single-linkage clustering | 0.8503 |
| SMTP protocol | | |
| Kulczynski coefficient | Zeta | 0.8437 |
| Czekanowski coefficient | Zeta | 0.8435 |
| Czekanowski coefficient | Single-linkage clustering | 0.7916 |

TABLE 4

| Attack name | n | False-positive rate |
| --- | --- | --- |
| HTTP protocol | | |
| HTTP tunnel | 2 | 0.0068 |
| IIS 4.0 htr exploit | 1-8 | 0.0000 |
| IIS 5.0 printer exploit | 1-8 | 0.0000 |
| IIS unicode attack | 1 | 0.0106 |
| IIS 5.0 webdav exploit | 1 | 0.0071 |
| IIS w3who exploit | 1-8 | 0.0000 |
| Nessus HTTP scan | 2 | 0.0128 |
| PHP script attack | 2 | 0.0060 |
| FTP protocol | | |
| 3COM 3C exploit | 2-4 | 0.0000 |
| GlobalScape 3.x exploit | 1-3 | 0.0000 |
| Nessus FTP scan | 1-3 | 0.0000 |
| ProFTPD 1.2.7 exploit | 6 | 0.4538 |
| Serv-U FTP exploit | 1-3 | 0.0000 |
| SlimFTPd exploit | 1-2 | 0.0000 |
| WarFTPd pass exploit | 1-4 | 0.0000 |
| WarFTPd user exploit | 1-3 | 0.0000 |
| WsFTPd exploit | 2-3 | 0.0000 |
| WU-FTPd exploit | 5 | 0.0529 |
| SMTP protocol | | |
| CMAIL Server 2.3 exploit | 1-4 | 0.0000 |
| dSMTP 3.1b exploit | 1 | 0.0643 |
| MS Exchange 2000 exploit | 1-5 | 0.0000 |
| MailCarrier 2.51 exploit | 2 | 0.0000 |
| Mail-Max SMTP exploit | 1-3 | 0.0000 |
| Nessus SMTP scan | 3 | 0.0000 |
| NetcPlus SmartServer3 exploit | 1-5, 7 | 0.0000 |
| Personal Mail 3.072 exploit | 1-5, 7 | 0.0000 |
| Sendmail 8.11.6 exploit | 5 | 0.0012 |

TABLE 5

| Kernel function | k(x, y) |
| --- | --- |
| Linear | $\sum_{\omega \in L} \phi_\omega(x)\phi_\omega(y)$ |
| Polynomial | $\left(\sum_{\omega \in L} \phi_\omega(x)\phi_\omega(y) + \theta\right)^d$ |
| RBF | $\exp\left(\frac{-d(x, y)^2}{\sigma}\right)$ |

TABLE 6

| Distance function | d(x,y) |
|---|---|
| Manhattan | $\sum_{\omega \in L} \|\phi_\omega(x) - \phi_\omega(y)\|$ |
| Canberra | $\sum_{\omega \in L} \frac{\|\phi_\omega(x) - \phi_\omega(y)\|}{\phi_\omega(x) + \phi_\omega(y)}$ |
| Minkowski | $\sqrt[k]{\sum_{\omega \in L} \|\phi_\omega(x) - \phi_\omega(y)\|^k}$ |
| Chebyshev | $\max_{\omega \in L} \|\phi_\omega(x) - \phi_\omega(y)\|$ |

TABLE 7

| Similarity coefficients | s(x, y) |
|---|---|
| Jaccard | $\frac{a}{a+b+c}$ |
| Czekanowski | $\frac{2a}{2a+b+c}$ |
| Sokal-Sneath | $\frac{a}{a+2(b+c)}$ |
| Kulsyznski | $\frac{1}{2}\left(\frac{a}{a+b} + \frac{a}{a+c}\right)$ |

TABLE 8

| Distance | ⊕ | $m^+(p, q)$ | $m_x^-(p)$ | $m_y^-(q)$ |
|---|---|---|---|---|
| Manhattan | + | \|p − q\| | p | q |
| Canberra | + | \|p − q\|/(p + q) | 1 | 1 |
| Minkowski$^k$ | + | \|p − q\|$^k$ | $p^k$ | $q^k$ |
| Chebyshev | max | \|p − q\| | p | q |

TABLE 9

| Variable | ⊕ | $m^+(p, q)$ | $m_x^-(p)$ | $m_y^-(q)$ |
|---|---|---|---|---|
| a | + | min(p, g) | 0 | 0 |
| b | + | p − min(p, q) | p | 0 |
| c | + | q − min(p, q) | 0 | q |

TABLE 10

| Name | Type | Alphabet | Min. length | Max. length |
|---|---|---|---|---|
| DNA | Human genome sequences | 4 | 2400 | 2400 |
| HIDS | BSM system call traces | 88 | 5 | 129340 |
| NIDS | TCP connection payloads | 108 | 53 | 132753 |
| TEXT | Reuters Newswire articles | 93 | 43 | 10002 |

TABLE 11

| | | | Average runtime for 5000 comparisons (s) | | | |
|---|---|---|---|---|---|---|
| Dataset | n | Trie | Hash ($10^2$) | Hash ($10^3$) | Hash ($10^4$) | Hash ($10^5$) |
| DNA | 3 | 0.19 | 0.22 | 0.28 | 0.66 | 6.04 |
| | 5 | 2.21 | 4.46 | 2.94 | 3.56 | 9.57 |
| | 7 | 10.72 | 37.63 | 13.02 | 5.67 | 9.43 |

TABLE 11-continued

| | | | Average runtime for 5000 comparisons (s) | | | |
|---|---|---|---|---|---|---|
| Dataset | n | Trie | Hash ($10^2$) | Hash ($10^3$) | Hash ($10^4$) | Hash ($10^5$) |
| HIDS | 3 | 0.06 | 0.10 | 0.13 | 0.62 | 3.05 |
| | 5 | 0.15 | 0.15 | 0.16 | 0.66 | 5.23 |
| | 7 | 0.25 | 0.19 | 0.22 | 0.70 | 4.15 |
| NIDS | 3 | 0.48 | 1.70 | 1.07 | 1.43 | 5.12 |
| | 5 | 0.86 | 3.70 | 1.72 | 1.81 | 5.90 |
| | 7 | 1.20 | 4.83 | 2.10 | 2.42 | 6.08 |
| TEXT | 3 | 1.12 | 1.75 | 1.22 | 1.63 | 7.03 |
| | 5 | 1.65 | 3.85 | 1.64 | 1.89 | 7.58 |
| | 7 | 2.13 | 5.92 | 2.19 | 2.24 | 7.74 |

TABLE 12

| Kernel function | k(x, y) |
|---|---|
| Linear | $\Sigma_{\omega \in L} \phi_\omega(x)\phi_\omega(y)$ |
| Polynomial | $(\Sigma_{\omega \in L} \phi_\omega(x)\phi_\omega(y) + \theta)^d$ |
| RBF | $\exp\left(\frac{-d(x, y)^2}{\sigma}\right)$ |
| Distance function | d(x, y) |
| Manhattan | $\Sigma_{\omega \in L} \|\phi_\omega(x) - \phi_\omega(y)\|$ |
| Canberra | $\sum_{\omega \in L} \frac{\|\phi_\omega(x) - \phi_\omega(y)\|}{\phi_\omega(x) + \phi_\omega(y)}$ |
| Minkowski | $\sqrt[k]{\Sigma_{\omega \in L} \|\phi_\omega(x) - \phi_\omega(y)\|^k}$ |
| Hamming | $\Sigma_{\omega \in L} \text{sgn}\|\phi_\omega(x) - \phi_\omega(y)\|$ |
| Chebyshev | $\max_{\omega \in L} \|\phi_\omega(x) - \phi_\omega(y)\|$ |

TABLE 13

| Similarity coefficient | s(x, y) |
|---|---|
| Simpson | a/min(a + b, a + c) |
| Jaccard | a/(a + b + c) |
| Braun-Blanquet | a/max(a + b, a + c) |
| Czekanowski, Sorensen-Dice | 2a/(2a + b + c) |
| Sokal-Sneath, Anderberg | a/(a + 2(b + c)) |
| Kulczynski (1st) | a/(b + c) |
| Kulczynski (2nd) | $\frac{1}{2}(a/(a+b) + a/(a+c))$ |
| Otsuka, Ochiai | $a/\sqrt{(a+b)(a+c)}$ |

TABLE 14

| | ⊕ | m(x, y) |
|---|---|---|
| Kernel function | | |
| Linear | + | x · y |
| Similarity coef. | | |
| Variable a | + | min(x, y) |
| Variable b | + | x − min(x, y) |
| Variable c | + | y − min(x, y) |
| Distance function | | |
| Manhattan | + | \|x − y\| |
| Canberra | + | \|x − y\|/(x + y) |
| Minkowski$^k$ | + | \|x − y\|$^k$ |

TABLE 14-continued

| | ⊕ | m(x, y) |
|---|---|---|
| Hamming | + | sgn\|x − y\| |
| Chebyshev | max | \|x − y\| |

TABLE 15

| Name | Type | Alphabet | Min. length | Max. length |
|---|---|---|---|---|
| DNA | Human genome sequences | 4 | 2400 | 2400 |
| NIDS | TCP connection payloads | 108 | 53 | 132753 |
| TEXT | Reuters Newswire articles | 93 | 43 | 10002 |

The invention claimed is:

1. A method for automatic byte stream comparison of at least two data sequences, a first and second data sequence comprising one or more of symbols, images, text, ASCII characters, genetic data, protein data, bytes, binary data, or tokens as objects are, the method comprising the steps of:
performing an evaluation of:
   a) a local relationship between any pair of subsequences in two or more sequences received from a byte stream, wherein subsequences for evaluation of the local relationship are specified on a com uterized detector by a subsequence selection mode comprising one of: words, wherein the words are subsequences separated by a given set of delimiters; n-grams, wherein the n-grams are overlapping subsequences of a given length n; and all possible subsequences of two or more sequences;
   b) performing an evaluation of a global relationship by aggregation of a plurality of evaluations of said local relationships, wherein evaluation of the global relationships is performed by one of the following data structures or a representation thereof: a hash table or indexed table; a trie or compacted trie; a suffix tree or suffix array; and a generalized suffix tree or generalized suffix array; and
   c) wherein the totality of local and global relationships comprises a measure s for similarity or dissimilarity of two or more sequences.

2. The method according to claim 1, wherein the totality of local and global relationships comprises one of the following similarity or dissimilarity measures s:
Manhattan or taxicab distance;
Euclidean distance;
Minkowski distance;
Canberra distance;
Chi-Square distance;
Chebyshev distance;
Geodesic distance;
Jensen or symmetric Kullback-Leibler divergence;
Position-independent Hamming distance;
$1^{st}$ and $2^{nd}$ Kulczynski similarity coefficient;
Czekanowski or Sorensen-Dice similarity coefficient;
Jaccard similarity coefficient;
Simpson similarity coefficient;
Sokal-Sneath or Anderberg similarity coefficient;
Otsuka or Ochiai similarity coefficient; and
Braun-Blanquet similarity coefficient.

3. The method according to claim 1, wherein the first and second data sequences (X, Y) each contain a plurality of objects to be detected;
a similarity measure s is automatically computed for subsequences in the first and second data sequences; and
depending on the similarity measure s, further processing steps are taken.

4. The method according to claim 3, wherein the first and second data sequences (X, Y) comprise data transmitted between computers in a computer network and depending on an on-line computation of the similarity measure s, at least one signal indicating an abnormal data stream or an intrusion is automatically generated.

5. The method according to claim 4, wherein the computers are part of a network for transmission of monetary information.

6. The method according to claim 1, wherein the first and second data sequences comprise one or more of genetic data, data exchanged between computers, text, image data, binary data, and symbols.

7. An apparatus for the comparison of data sequences comprising:
a computerized storage device programmed for representing data sequences in a data structure selected from one of:
a hash table or indexed table;
a trie or compacted trie;
a suffix tree or suffix array; and
a generalized suffix tree or generalized suffix array;
a computer processor for performing an evaluation of a local relationship between any pair of subsequences in said data sequences;
a computer processor for performing an evaluation of a global relationship by aggregation of a plurality of evaluations of said local relationships;
a computer processor for computation of a totality of the local and global relationship, wherein at least one of the first and second data sequences comprise one or more of symbols, images, text, ASCII characters, genetic data, protein data, bytes, binary data, or tokens as objects for which the local relationship is evaluated; and
a computer processor for generating from the totality of local and global relationships a measure s for similarity or dissimilarity of two or more sequences.

8. A system for processing and analysis of data sequences comprising:
means for input of data sequences comprising a data structure selected from one of:
a hash table or indexed table;
a trie or compacted trie;
a suffix tree or suffix array; and
a generalized suffix tree or generalized suffix array, means for comparison of data sequences comprising one of:
Manhattan or taxicab distance;
Euclidean distance;
Minkowski distance;
Canberra distance;
Chi-Square distance;
Chebyshev distance;
Geodesic distance;
Jensen or symmetric Kullback-Leibler divergence;
Position-independent Hamming distance;
1st and 2nd Kulczynski similarity coefficient;
Czekanowski or Sorensen-Dice similarity coefficient;
Jaccard similarity coefficient;
Simpson similarity coefficient;
Sokal-Sneath or Anderberg similarity coefficient;
Otsuka or Ochiai similarity coefficient; and
Braun-Blanquet similarity coefficient, means for analysis of data sequences including classification, regression, novelty detection, ranking, clustering, and structural inference;

means for reporting of results of the analysis: and means for generating from the totality of local and global relationships a measure s for similarity or dissimilarity of two or more sequences.

* * * * *

UNITED STATES PATENT AND TRADEMARK OFFICE
CERTIFICATE OF CORRECTION

PATENT NO.      : 8,271,403 B2
APPLICATION NO. : 12/096126
DATED           : September 18, 2012
INVENTOR(S)     : Konrad Rieck et al.

Page 1 of 1

It is certified that error appears in the above-identified patent and that said Letters Patent is hereby corrected as shown below:

Column 33, Line 28, Claim 1, delete "com uterized" and insert -- computerized --

Column 35, Line 4, Claim 8, delete "analysis:" and insert -- analysis; --

Signed and Sealed this
Thirteenth Day of November, 2012

David J. Kappos
*Director of the United States Patent and Trademark Office*